(12) United States Patent
Coleman

(10) Patent No.: US 7,820,594 B2
(45) Date of Patent: Oct. 26, 2010

(54) PESTICIDE COMPOSITIONS AND METHODS FOR THEIR USE

(76) Inventor: Robert D. Coleman, 7723 Kempfer La., Verona, WI (US) 53593

( * ) Notice: Subject to any disclaimer, the term of this patent is extended or adjusted under 35 U.S.C. 154(b) by 115 days.

(21) Appl. No.: 11/767,829

(22) Filed: Jun. 25, 2007

(65) Prior Publication Data
US 2007/0249699 A1    Oct. 25, 2007

Related U.S. Application Data

(63) Continuation-in-part of application No. 10/501,026, filed on Jul. 9, 2004, and a continuation-in-part of application No. PCT/US03/00608, filed on Jan. 9, 2003.

(51) Int. Cl.
| | | |
|---|---|---|
| A01N 25/00 | (2006.01) | |
| A01N 37/00 | (2006.01) | |
| A01N 65/00 | (2006.01) | |
| A01N 33/18 | (2006.01) | |
| A01N 25/24 | (2006.01) | |
| A01N 25/34 | (2006.01) | |
| A01N 29/02 | (2006.01) | |
| A61K 31/01 | (2006.01) | |
| A61K 31/02 | (2006.01) | |
| A61K 47/00 | (2006.01) | |
| A61K 31/04 | (2006.01) | |

(52) U.S. Cl. ............... 504/116.1; 504/189; 504/320; 514/740; 514/741; 514/761; 514/762; 514/784; 514/789; 424/404; 424/405; 424/407

(58) Field of Classification Search ............. 504/116.1, 504/189, 320
See application file for complete search history.

(56) References Cited

U.S. PATENT DOCUMENTS

| | | | |
|---|---|---|---|
| 3,947,589 A | | 3/1976 | Misato et al. |
| 4,430,381 A | | 2/1984 | Harvey et al. |
| 4,436,547 A | | 3/1984 | Sampson |
| 4,581,373 A | | 4/1986 | Mulqueen et al. |
| 4,599,233 A | | 7/1986 | Misato et al. |
| 5,035,741 A | | 7/1991 | Puritch et al. |
| 5,078,782 A | | 1/1992 | Nielsen et al. |
| 5,093,124 A | | 3/1992 | Kulenkampff |
| 5,106,410 A | * | 4/1992 | Puritch et al. .............. 504/142 |
| 5,123,950 A | | 6/1992 | Homma et al. |
| 5,143,718 A | | 9/1992 | Bar-Shalom |
| 5,246,716 A | | 9/1993 | Sedun et al. |
| 5,248,694 A | | 9/1993 | Homma et al. |
| 5,366,995 A | * | 11/1994 | Savage et al. .............. 514/558 |
| 5,496,568 A | | 3/1996 | Winston |
| 5,518,986 A | | 5/1996 | Winston |
| 5,518,987 A | | 5/1996 | Winston |
| 5,573,997 A | | 11/1996 | Lojek |
| 5,741,502 A | * | 4/1998 | Roberts ...................... 424/405 |
| 5,756,128 A | | 5/1998 | Arimoto |
| 5,849,663 A | | 12/1998 | Hasebe et al. |
| 5,863,909 A | | 1/1999 | Kurita et al. |
| 5,998,358 A | | 12/1999 | Herdt et al. |
| 6,008,158 A | | 12/1999 | Hasebe et al. |
| 6,039,966 A | | 3/2000 | Kostka et al. |
| 6,180,566 B1 | * | 1/2001 | Nielsen et al. ............. 504/206 |
| 6,218,336 B1 | | 4/2001 | Coleman |
| 6,291,401 B1 | | 9/2001 | DuFau et al. |
| 6,509,297 B1 | | 1/2003 | Coleman |
| 2003/0224938 A1 | | 12/2003 | Coleman |

FOREIGN PATENT DOCUMENTS

| | | | |
|---|---|---|---|
| SU | 0844584 | | 7/1981 |
| WO | WO 91/13552 | * | 9/1991 |

OTHER PUBLICATIONS

The definite of Fatty Acid (retrieved from Wikipedia online via http://en.wikipedia.org/wiki/Fatty_Acid).*

* cited by examiner

*Primary Examiner*—Johann R Richter
*Assistant Examiner*—Mei-Ping Chui
(74) *Attorney, Agent, or Firm*—Edward E. Sowers; Brannon & Sowers PC

(57) ABSTRACT

This invention relates to agricultural compositions, particularly pesticidal compositions which find particular use as a fungicide or herbicide composition. The pesticidal composition can include one or more fatty acids and one or more organic acids different from the fatty acid. The organic acid can but need not exhibit any fungicidal activity; however, when combined with a fatty acid, the organic acid functions as a potent synergist for the fatty acid as a fungicide. Additionally, the pesticidal composition can include other components such as emulsifiers, adjuvants, surfactants and diluents. The pesticidal composition significantly reduces or prevents the fungal infection of cash crops including vegetables, fruits, berries, seeds, grains and at higher application rates, can also be used as a herbicide and/or harvest aid or desiccant for harvested crops such as potatoes. The addition of an emulsifier further enhances the herbicidal properties of the compositions.

40 Claims, No Drawings

US 7,820,594 B2

PESTICIDE COMPOSITIONS AND METHODS FOR THEIR USE

CROSS REFERENCE TO RELATED APPLICATIONS

The present application is a continuation-in-part of U.S. application Ser. No. 10/501,026 filed on Jul. 9, 2004, and a continuation-in-part of PCT application No. PCT/US2003/00608 filed on Jan. 9, 2003, which are hereby incorporated by reference in their entirety.

BACKGROUND OF THE INVENTION

The present invention relates to pesticide compositions and methods for treating plants and agricultural products.

Agricultural crops dependent on the growth and maintenance of plants are subject to a variety of agricultural pests which can destroy and/or reduce crop yields. Damage to plants can result from microorganisms such as fungi or from more vigorous plants better able to compete for space and nutrients.

Fungus can often attack and destroy crops and, if not kill them, can induce distress in the crops so that they succumb to other diseases and/or significantly lower crop yield. Furthermore, agricultural products can be particularly susceptible to damage by fungus after the products are harvested. Many of the products are stored for extended periods of time before they reach the consumer or are used by the consumer. The fungus can make the harvested agricultural products inedible or otherwise unusable. This can be particularly problematic since a significant amount of effort and money has gone into producing and harvesting the agricultural products; all of this can be lost before the products reach the consumer.

Consequently, it is not surprising that there are many fungicide compositions currently on the market. However, there is a growing concern that some of these compositions, one or more of their components, and/or metabolites eventually find their way into the food sources for animals, including humans. Unfortunately, many fungicides and/or their byproducts are moderately and even extremely toxic. Further, some fungicides are suspected or known carcinogens. Despite this fact, many fungicides continue to be used and are needed to protect cash crops. It is important to note that some fungi are themselves extremely toxic or produce toxic components. For example, aflatoxins belong to a class of fungal metabolites and are known to occur naturally in many products including peanuts, cottonseed, corn, peppers, etc. Many aflatoxins are extremely toxic and some are listed as known carcinogens. Consequently, fungicides are needed to protect and preserve agricultural products and ensure the public's health.

Similarly, more vigorous wild plants generally referred to as weeds, can compete with a crop plant, reduce its vigor, reduce yields and in many instances kill crop plants. Selective herbicides can be used to kill unwanted plants growing about a crop plant without damaging crop plants. Non-selective herbicides are typically used to control weeds and unwanted plants prior to planting a crop and in non-agricultural settings. As used herein, herbicidal refers to materials which destroy or inhibit plant growth, whereas harvest aids desiccate or defoliate non-harvestable portions of crop plants such as potato, dry bean and cotton.

Glyphosate and paraquat are the number 1 and 2 non-selective herbicides used worldwide. Paraquat is extremely toxic and therefore unacceptable for many applications. Glyphosate can be slow acting, commonly requiring 1 to 2 weeks to achieve plant death and therefore can be unsuitable for many herbicide applications.

Other conventionally known herbicides include Scythe (Dow AgroScience), containing pelargonic acid, a nine carbon fatty acid and Liberty made by AgrEvo. Pelargonic acid is the active ingredient in SCYTHE and glufosinate-ammonium is the active ingredient in LIBERTY. However, the activity of these products is such that the cost of products such as SCYTHE can be undesirably high and the amount of active ingredients needed in products such as paraquat could lead to undesirable effects.

Consequently, with increased demand and necessity for agricultural products to feed and clothe the world population, and with the risks associated with eating and using diseased products, there is an increased need in the field for advancements in new pesticides. These advancements include improved methods and compositions for treating plants, particularly cash crops and products derived from the plants and for controlling the unwanted growth of non-crop plants. The present invention is such an advancement and provides a wide variety of benefits and advantages.

SUMMARY

The present invention relates to novel agricultural compositions and use thereof. Various aspects of the invention are novel, non-obvious, and provide various advantages. While the actual nature of the invention covered herein can only be determined with reference to the claims appended hereto, certain forms and features, which are characteristic of the preferred embodiments disclosed herein, are described briefly as follows.

The compositions described herein function as fungicides and/or herbicides, including crop desiccants. The compositions include a fatty acid, or a salt thereof having between 5 and 22 carbon atoms included in a pesticidally effective amount; an organic carboxylic acid, or a salt thereof, different from the fatty acid, an emulsifier; and optionally, an additive.

In one form, the present invention provides a composition comprising a combination of a fatty acid species or a salt thereof, and an organic acid species or a salt thereof, different from the fatty acid and its salts. In preferred embodiments, the composition also includes a wide variety of additives including one or more of emulsifiers, adjuvants, diluents, dispersants, and/or surfactants, to name just a few.

The pesticide can be formulated as a liquid concentrate that can be diluted with water to yield a ready-to-use formulation suitable for application to the locus of plants, their fruit, vegetable, seeds and/or nuts or for application to unwanted weed species and/or crops prior to or after harvest. The concentrate or the ready-to-use formulation can be supplied as an aqueous solution, a suspension, or an emulsion. The ready-to-use formulation can include additional components including, for example, one or more emulsifiers selected to suspend the fatty acid and/or the organic acid in water, and be specifically formulated to target either a particular plant species weed or crop and/or a particular pathogen.

In selected embodiments, the fatty acid species can be selected as a fatty monocarboxylic acid, having between 2 and 22 carbons. The fatty acid species can be saturated or unsaturated. Preferred fatty acids include, but are not limited to fatty acids selected from the group consisting of: acetic acid, arachidic acid, arachidonic acid, behenic acid, butyric acid, decanoic acid, erucic acid, heptanoic acid, hexanoic acid, lauric acid, linoleic acid, linolenic acid, margaric acid, myristic acid, nonanoic acid, octanoic acid, oleic acid, palmitic acid, palmitoleic acid, pentadecanoic acid, pentanoic acid, propionic acid, stearic acid, undecanoic acid, mixtures thereof. More preferred fatty acids include nonanoic acid and octanoic acid.

The organic acids utilized can include, but are not limited to monocarboxylic acids, dicarboxylic acids, aromatic carboxylic acids, hydroxyl substituted carboxylic acids and mixtures thereof. In the selected embodiments, preferred organic carboxylic acids include, but are not limited to organic carboxylic acids selected from the following group of acids: alanine, arginine, aspartic acid, ascorbic acid, asparagine, benzoic acid, bionic acids, cinnamic acid, citric acid, cysteine, formic acid, fulvic acid, fumaric acid, galactonic acid, gluconic acid, glutamic acid, glutamine, gluconic acid, glutaric acid, glyceric acid, glycine, glycolic acid, hexonic acid, histidine, humic acid, isobutyric acid, isocitric acid, isoleucine, itaconic acid, ketoglutaric acid, lactic acid, leucine, lysine, methionine, mevalonic acid, malonic acid, oxalacetic acid, pentonic acid, phenylalanine, proline, propionic acid, pyruvic acid, proline, trichloroacetic acid, tetrahydrofurfuryl salicylic acid, saccharic acid, salicylic acid and other salts of salicylic acid, serine, succinic acid, tartaric acid, threonine, tryptophan, tyrosine, valine and mixtures thereof. More preferred organic acids include, citric acid, gluconic acid, glycolic acid, lactic acid, propionic acid, succinic acid, tartaric acid, and mixtures of these acids. Any of the compositions described above can further include an adjuvant and/or a diluent.

In still yet another form, the present invention provides a method of controlling fungus, said method comprising contacting one or more of plants, fruit, vegetables, seeds, and nuts with an effective amount of a ready-to-use composition prepared by diluting with water the concentrate listed above.

In still yet another form, the present invention provides a method of treating a crop product, said method comprising applying to the crop product a fungicidal composition comprising a fungicidally active amount of a fatty acid, having between 5 and 22 carbon atoms and an organic acid different from the fatty acid.

In still yet another form, the present invention provides a method of controlling the growth of unwanted plants typically described as weeds, said method comprising contacting one or more of plants, with an effective amount of a herbicidally active amount of a fatty acid, or salt thereof, having between 5 and 22 carbon atoms, an organic acid, or salt thereof, different from the fatty acid, an emulsifier, and an additive selected from the group consisting of an adjuvant, a diluent, and a combination thereof.

In still yet another form, the present invention provides a method of desiccating a crop to aid harvest, said method comprising contacting one or more of plants, with an effective amount of a herbicidally active amount of a fatty acid, or salt thereof, having between 5 and 22 carbon atoms, an organic acid, or salt thereof, different from the fatty acid, an emulsifier, and an additive selected from the group consisting of an adjuvant, a diluent, and a combination thereof.

In still yet another form, the present invention provides a method of controlling the growth of unwanted plants typically described as weeds, said method comprising contacting one or more of plants, with an effective amount of a ready-to-use composition prepared by diluting with water the concentrate listed above.

In still yet another form, the present invention provides a method of desiccating a crop to aid harvest, said method comprising contacting one or more of plants, with an effective amount of a ready-to-use composition prepared by diluting with water the concentrate listed above.

DETAILED DESCRIPTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described compositions, methods, or systems, and any further applications of the principles of the invention as described herein, are contemplated as would normally occur to one skilled in the art to which the invention relates.

In general, the present invention is directed to an agricultural composition particularly useful for treating plants under cultivation, agricultural products, produce, grains, cash crops, or other stable crops. The present composition finds particularly useful advantages as a fungicide, as a herbicide, and as a crop desiccant. The agricultural composition can include one or more fatty acids in combination with one or more organic acids that is/are different from the fatty-acid. The composition can be provided either as a liquid concentrate or a ready-to-use formulation. The ready-to-use formulation can be a clear, aqueous solution, a suspension, or an emulsion.

In particularly preferred embodiments, the agricultural composition includes additional components such as emulsifiers, diluents, adjuvants, dispersants, and/or surfactants. The agricultural composition can be applied to the locus of plants and/or to the agricultural products. For example, the agricultural composition can be applied either as a pre-emergent, post-emergent, foliar or post-harvest application. Additionally, the composition can be applied to agricultural products or crop products such as fruits, nuts, berries, vegetables, grains, seeds, stems, bark, leaves, or any other component derived from the plant either before or after harvesting the products. When applied to an agricultural product, the composition can be provided either as a spray or a dipped solution and can be used as a single or multiple treatment application. The agricultural composition can be used and applied prophylactically or to treat an emerging or existing fungicide infection.

The agricultural composition can include one or more fatty acids. The fatty acid can be selected from a wide variety of fatty acids commercially available and/or widely known to those skilled in the art. In preferred embodiments, the fatty acid is selected to prevent, inhibit and/or retard fungal infections or fungal growth on plants. The fatty acids are aliphatic hydrocarbons with a terminal carboxylic acid functionality. Preferred examples of fatty acids include aliphatic, saturated, or unsaturated monocarboxylic fatty acids having between 5 and 22 carbon atoms. More preferably, the fatty acids are selected to have between 7 and 10 carbon atoms.

Preferably, fatty acids are selected which, upon incorporation into a pesticide composition provides a composition which can prevent, inhibit and/or retard fungal infections or which can kill or desiccate plants treated with the composition. Retardation or inhibition of fungal infections can be determined by a variety of commonly known evaluations. For example, the growth rate of fungi, measured in surface area of plant leaves or stems, can be measured and monitored over time. Consequently, it has been determined that certain fatty acids prevent, inhibit/retard fungal infections better than other fatty acids. Not to be limiting in any manner, it has been determined, for example, that fatty acids having 8 carbon atoms inhibit Botrytis cinerea on raspberries better than acids having 7 carbon atoms, which are better than acids having 9 carbon atoms, which are better than acids having 10 carbon atoms, all of which are better than acids having 6 carbon atoms. Similarly, the herbicidal/desiccant properties of compositions can be determined by commonly known evaluations.

Specific examples of available fatty acids for use in the present invention include, but are not limited to, arachidic acid, arachidonic acid, behenic acid, decanoic acid (n-capric acid), erucic acid, heptanoic acid (enanthic acid), hexanoic acid, 2-hexyldecanoic acid, lauric acid, linoleic acid, linolenic acid, margaric acid, myristic acid, nonanoic acid (pelargonic acid), octanoic acid (caprylic acid), oleic acid, palmitic acid, palmitoleic acid, pentadecanoic acid, pentanoic acid, soya fatty acids, stearic acid, undecanoic acid, and the like.

The fatty acid is included in the agricultural composition in a desired amount; preferably in a fungicidally effective amount sufficient to elicit prevention or inhibition of fungal growth. In preferred embodiments of fungicidal compositions, a concentrated formulation of the agricultural composition comprises between about 1% v/v and about 99% v/v of a fatty acid; more preferably, between about 20 and about 90% v/v based upon the total volume of the concentrated formulation. In preferred embodiments of herbicidal/desiccant compositions, a concentrated formulation of the agricultural composition comprises between about 30% v/v and about 99.5% v/v of a fatty acid; more preferably, between about 40 and about 95% v/v based upon the total volume of the concentrated formulation.

The agricultural composition also includes an organic acid that is different from the fatty acid. The organic acid can be selected from a wide variety of known and commonly used acids. The organic acid, in combination with one or more fatty acid(s) in the pesticidal compositions, promotes additional or a synergistic pesticidal activity over that exhibited by the fatty acid(s) used individually or with one of the other additives. The organic acid can be selected to include acids having between 2 and 20 carbon atoms. The organic acids can be selected to be an aliphatic, saturated or unsaturated, cyclic, and/or aromatic. The acids can be mono acids, diacids, triacids, ketoacids, sugar acids, or hydroxy acids, each of which can be substituted with one or more oxygen, hydroxy groups, nitrogen, halide, or hydroxyl, halide, oxygen and nitrogen, or hydroxyl, halide, oxygen, nitrogen, amine, sulfur, phosphate, carboxyl substituents.

Specific examples of readily available organic acids for use in fungicidal compositions include, but are not limited to, acrylic acid, alanine, arginine, asparagine, aspartic acid, benzoic acid, cinnamic acid, cysteine, diethylamine salicylic acid, formic acid, fulvic acids, fumaric acid, glutamic acid, glutamine, glutaric acid, glyceric acid, glycine, glycolic acid, histidine, humic acid, isobutyric acid, isocitric acid, isoleucine, itaconic acid, ketoglutaric acid, lactic acid, leucine, lysine, malonic acid, methionine, mevalonic acid, oxalacetic acid, phenylalanine, proline, propionic acid, pyruvic acid, serine, sugar acids [such as bionic acids (i.e., saccharic acid and ascorbic acid), hexonic acid (i.e., gluconic acid and galactonic acid), and pentonic acid (i.e., ribonic acid and xylonic acid),], tetrahydrofurfuryl salicylic acid, threonine, trichloroacetic acid, tryptophan, tyrosine, valine, and mixtures of these acids. Specific examples of readily available fatty acids for use in herbicidal/desiccant compositions include, but are not limited to acetic acid, arachidic acid, arachidonic acid, behenic acid, butyric acid, decanoic acid, erucic acid, heptanoic acid, hexanoic acid, lauric acid, linoleic acid, linolenic acid, margaric acid, myristic acid, nonanoic acid, octanoic acid, oleic acid, palmitic acid, palmitoleic acid, pentadecanoic acid, pentanoic acid, propionic acid, stearic acid, undecanoic acid, mixtures thereof.

Fungicidal Compositions and Methods for their Use

A "ready-to-use formulation" of the agricultural composition (a concentrated formulation that is diluted in water or other diluent such as seed oil, ethanol, etc.) having fungicidal properties can include the organic acid species together with one or more fatty acid(s) in an amount sufficient to induce prevention, inhibition or retardation of fungal infection and comprises an amount of the fatty and organic acids less than the amount that will inhibit plant growth. In preferred embodiments, a ready-to-use formulation for use in the present invention comprises at least about 0.001% v/v, of fatty and organic acids; more preferably at least about 0.05% v/v; and still yet more preferably at least about 0.10% v/v of the fatty acid and organic acid, based upon the total volume of the formulation.

The agricultural composition can include both the fatty acids species and the organic acid species, different from the fatty acid species in a wide range of ratios. In preferred embodiments, the ratio of fatty acid species to organic acids species is in a weight ratio of between 1:1000 to about 1000:1. More preferably, the weight ratio of fatty acid species to organic acid species is between about 1:5 to about 5:1. The agricultural composition for use in the present invention can be prepared by admixing all desired ingredients at the same time.

Alternatively, the fatty acid species can be premixed with one or more additives such as an adjuvants, surfactants, emulsifiers, and/or diluents in water. When premixed, the ratio of fatty acid to additive(s) can be between about 1:5 to about 1000:1. The fatty acid and additive(s), either singly or as a combined pre-mix, can be suitably dissolved in a solvent such as water, alcohol, and/or an organic solvent, such as an oil or ketone, suitable for treatment of agricultural products or plants.

In preferred embodiments, either the concentrate or the ready-to-use formulation is admixed with a variety of additives; for example, adjuvants, surfactants, emulsifiers, and/or diluents. The additive can be selected from a wide variety of known commercially available products. Typical adjuvants, surfactants, and/or emulsifiers (either synthetic or natural emulsifiers) for use with fatty acids include, for example: organosilicones (i.e., Sylgard 309 sold by Dow Corning Corp, Kinetic, Silwet L77), methylated seed oil, and ethylated seed oil (i.e., Scoil sold by Agsco or Hasten sold by Wilfarm), alkylpolyoxyethylene ethers (i.e., Activator 90), alkylarylalolates (i.e., APSA 20), alkylphenol ethoxylate and alcohol alkoxylate surfactants (i.e., products sold by Huntsman), fatty acid and fatty amine ethoxylates (i.e., products sold by Huntsman), anionic surfactants such as sulfosuccinates, sulfonates, and phosphate esters (such as products sold by Huntsman Chemical or BASF), polyethylene glycol (PEG) fatty acid esters and alkyl napthalene sulfonates (i.e., products sold by Adjuvants Unlimited), tristyrylphenol, castor, oil and fatty amine ethoxylates and products sold by Cognis such as sorbitan and ethoxylated sorbitan esters, ethoxylated alcohols and alkylphenols, ethoxylated vegetable oils, alkyl, glycol and glycerol esters. Also to be included are natural emulsifiers such as lecithin. Examples of diluents include mineral oil and natural oils such as vegetable oil, coconut oil, olive oil, corn oil, canola oil, cottonseed oil, and soybean oil, to name just a few.

In selected embodiments, a "ready-to-use formulation" (i.e., a concentrated formulation diluted in water or other solvent) as a fungicide, according to the present invention contains between about 0.001% v/v and about 3% v/v fatty acid, more preferably between about 0.005% v/v and about 2.0% v/v of the fatty acid, still more preferably between about 0.01% v/v and about 1.0% v/v of the fatty acid. The organic acid is included in an amount between about 0.001% v/v and about 4% v/v; more preferably, between about 0.1% v/v and about 1% v/v (or wt/vol, for solid organic acids). When used as a foliar spray application treatment, the fungicide composition can be directly applied to the crop products; i.e., leaves, fruit or other crops, such as fruit, vegetables, berries, nuts, seeds, and the like. Furthermore, in use, the fungicide composition can be applied as a single use or single treatment, or in multiple treatments.

In other embodiments, the fungicide composition can be combined with one or more other treatment processes and compositions. For example, the fungicide composition can be combined with a herbicide composition, a desiccant composition, or an insecticide composition. A combination of the fungicide with one or more other treatment compositions and applications obviously reduces treatment costs and consequently can improve efficiency of operation.

In preferred embodiments, the selected combination of a fatty acid species and an organic acid species exhibits unexpected results or synergism by providing improved fungicidal activity over any of the individual components by themselves. The organic acid, alone, has little or no fungicidal activity; however, when combined with the fatty acid, a strong synergism results.

The crop products can be selected from any commonly known or used cash crops including fruits, vegetables, berries, nuts, leaves, seeds, grains and the like. Specific examples in which the fungicide composition finds particular use include crops, strawberries, raspberries, blueberries, melons, stone fruit, nut crops, potatoes, vegetables, turf grasses, seed crops (i.e., seed grasses, alfalfa seed), corn, rice, wheat, soybeans, dry beans, peanuts, cotton, sorghum, and other row crops, curcurbits, other small fruit crops, and horticultural plants.

The fungicide composition can be provided to the end user either as a liquid concentrate or in a "ready-to-use composition" (i.e., a concentrated formulation diluted in water or other diluent). When provided as a liquid concentrate, the fungicide composition includes the fatty acid species in a range, of between about 1% v/v and about 99% v/v, the organic acid species in a range between about 0.1% v/v and about 90% v/v, and the additives in a range between about 0.01% v/v and about 80% v/v.

In another embodiment, the fungicide composition can be provided as: (a) a harvest aid to desiccate foliage, stems, and/or vines prior to harvest crops such as seed grasses, onions, potatoes, cotton, and dry beans, or (b) a preservative to treat and/or preserve the harvested crops such as fruits, vegetables, berries, nuts, leaves, seeds, grains, and the like. When provided as a preservative, the fungicide composition can be applied either as a spray or as a dip solution. When provided as a dip solution, the fungicide composition can be used in a large vat in which the harvested crop is dipped into the liquid composition. Thereafter, the submerged crop is removed from the fungicide composition and allowed to drain followed by drying. The dried product can then be safely stored for use at a later time. Furthermore, when used as a preservative, the fungicide composition can be used immediately after harvest or most any time subsequent to harvesting.

The fungicide composition exhibits a broad range of fungicide activity against a large number of target pathogens. Non-limiting examples of specific pathogens targeted by the fungicide composition include: *Altemaria* sp. (i.e., Alternaria fruit rot), *Alternaria solani* (early blight, potatoes), *Arthuriomyces* sp. (i.e., powder mildew), *Apiosporina morbosa* (i.e., black knot of stone fruit), *Aspergillus* sp. (i.e., *Aspergillus paraciticus*, black rot of apple, blossom end rot of apple, blue mold of apple, brown rot of stone fruit, *Blumeriella jaapii* (i.e., cherry leaf spot of stone fruit), *Botrytis cinerea* (i.e., Botrytis bunch rot, gray mold, *Botrytis* blight), *Colletotrichum acutatum* (i.e., anthracnose fruit rot), *Dendrophoma obscurans* (i.e., stem end rot, leaf blight), *Diplocarpon earliana* (i.e., leaf scorch), *Drepanopeziza* sp. (i.e., anthracnose), *Exobasidium vaccinii* (i.e., red leaf disease), *Fusarium* sp. *Septoria* sp., *Godronia cassandrae* (i.e., fusicoccum canker), *Guignardia bidwellii* (i.e., black rot), *Gymnosporangium* sp. (i.e., apple rust), *Kuehneola* sp. (i.e., cane and leaf rust), *Leucostoma cincta* or *Leucostoma persoonii* (i.e., cytospora canker of stone fruits), *Microsphaera vaccinii* (i.e., powdery mildew), *Monilinia fructicola* (i.e., brown rot of stone fruit), *Monilinia vacinii-corymbosi* (i.e., mummy berry), *Mycosphaerella* sp. (leaf spot), *Phomopsis viticola* (i.e., Phomopsis cane and leaf spot), *Phomopsis rachis, Phomopsis vaccinii* (i.e., Phomopsis twigblight and canker), downy mildew, *Phragmidium sp.* (i.e., yellow rust), *Phytophthora cactorum* (i.e., leather rot), *Phytophthora fragariae* (i.e., red stele root rot), *Phytophthora infestans* (late blight, potatoes), *Podosphaera leucotricha* (i.e., apple powdery mildew), *Pythium ultimatum, Rhizopus sp.*, white rot of apple, sooty mold of pear, pear leafspot, pear leaf blight and fruit spot, *Rhizoctonia solani* (i.e., black scurf in potatoes, aerial blight, soybeans), *Sclerotium rolfsii* (i.e., Sclerotium rot, sugar beets), *Sphaerotheca macularis* (i.e., powdery mildew), *Sphaerulina* sp. (i.e., orange rust), *Verticillium albo-atrum* (i.e., Verticillium wilt), *Venturia inaequalis* (i.e., apple scab), and white mold in soybeans and the like.

For the purpose of promoting further understanding and appreciation of the present invention and its advantages, the following examples directed to fungicidal compositions and methods for their use are provided. It will be understood, however, that these examples are illustrative and not limiting in any fashion. Unless specifically indicated to the contrary, all percentages listed below in the following examples are percentage by volume, based upon the total volume of the resulting composition.

EXAMPLE 1

Retardation of White Mold Growth on Soybean Foliage

Soybean foliage was treated with caprylic acid with a solution that contains sorbitan monolaurate, sold under the trade name Emsorb 6915 by Cognis, and mineral oil. A stock solution of the caprylic acid was formulated to include about 0.75% caprylic acid, about 1% HASTEN (or 0.5% Sylgard 309), about 0.21% sorbitan monolaurate, and about 0.11% mineral oil by volume percent. This was applied to plants at 40 gallons per acre (gpa). The plants were about 9-12 inches in height. Foliage from the plants was collected at days 2, 4, 7, and 34 after fungicide treatment, washed in warm water, drained, and then inoculated with the mold inoculum. White mold inoculum (5 mm diameter plugs) was used to infect the foliage of soybean plants (species GL2415). The inoculated foliage was incubated for 2-3 days at room temperature (at 100% humidity) under fluorescent lighting. The results are listed below in Table 1.

TABLE 1

| Treatment Solution | Average radii of fungal growth[1] at days after fungicide treatment: | | | |
|---|---|---|---|---|
| | 2 | 4 | 7 | 34 |
| Control (untreated) | 100 | 100 | 100 | 100 |
| 0.21% 6915 + 0.11% mineral oil + 0.75% caprylic acid + 1% HASTEN | 50 | 44 | 52 | * |
| 0.29% 6915 + 0.14% mineral oil + 1% caprylic acid + 1% HASTEN | 55 | 45 | 35 | * |
| 0.21% 6915 + 0.11% mineral oil + 0.75% caprylic acid + 0.5% SYLGARD | 46 | 47 | 26 | 66 |
| 0.29% 6915 + 0.14% mineral oil + 1% caprylic acid + 0.5% SYLGARD | 53 | 29 | 38 | 67 |

[1]Fungal growth for Control (treatment 1) is expressed as 100%.

From the results listed above, it can be determined that even as little as 0.75% caprylic acid demonstrated significant reduction in the fungal growth on soybean foliage.

EXAMPLE 2

Retardation of White Mold Growth on Soybean Foliage

The foliar treatments were applied at a rate of 40 gpa (40 psi) to 4 soybean plants (15-20" in height) per each treatment group (Table 2). Two leafs/plant were used for the detached leaf assay. White mold inoculums (5 mm plugs from potato dextrose agar plates) were used to inoculate soybean foliage (species GL 2415). Foliage from the soybean plants were washed in warm water, drained, collected and inoculated and the inoculated foliage was incubated for 3 days at room temperature (100% humidity) under fluorescent lighting. The results are listed in Table 2 below.

TABLE 2

| Treatment Solution | Average Radii (mm)[2] | Percent Fungal Growth Based on Control |
|---|---|---|
| Control (untreated) | 3.14 | 100% |
| 0.21% 6915[1] + 0.11% mineral oil | 3.012 | 96 |
| 0.2% 6915[1] + 0.11% mineral oil + 0.75% caprylic acid | 2.225 | 71 |
| 0.07% 6915[1] + 0.04% mineral oil + 0.25% caprylic acid | 2.75 | 88 |
| 0.02% 6915[1] + 0.01% mineral oil + 0.08% caprylic acid | 2.813 | 90 |

[1]Cognis Emsorb 6915
[2]Average radii (mm) of fungal growth on leaf surface measured at day 3

From the results listed in Table 2 it can be demonstrated that caprylic acid significantly inhibits the fungal growth of white mold on soybean foliage. The orthogonal comparison of the control and the treatment containing 0.75% caprylic acid was statistically significant at P>0.95, and orthogonal comparison of the treatment solution containing 0.21% 6915 and 0.11% mineral oil versus treatment solution containing 0.2% 6915, 0.11% mineral oil, 0.75% caprylic acid indicated statistical significance at P>0.90.

EXAMPLE 3

Reduction of Phytophthora Infestans on Potato Foliage at 1 and 10 Days After Treatment Snowden potatoes were grown in Baccto potting soil to a height of 14-21 inches. All plants were fertilized one time per week. The plants were then treated as listed below in Table 3. The treatment solutions listed below in Table 3 were applied at 40 gpa (40 psi) to three plants (3 plants per treatment group). Each treatment included 0.2% SYLGARD 309 sold by Dow Corning. At one and ten days after treatment, foliage (4 leafs per plant) were washed in warm water, drained and inoculated. The inoculated foliage was incubated for 2-3 days at room temperature (100% humidity) via fluorescent lighting. *P. infestans* plugs from PDA plates were used to inoculate 4 leaves/plant. The results are listed below in Table 3.

TABLE 3

| Treatment Solution | Average radii (mm) of Growth (*P. infestans*) Day 1 | | Day 10 | |
|---|---|---|---|---|
| 0.57% 6915[1] + 0.29% mineral oil | 9.49 | 100% | 8.35 | 100% |
| 0.57% 6915[1] + 0.29% mineral oil + 2% caprylic acid | 1.24 | 13%[2] | 1.35 | 16%[3] |

[1]Cognis Emsorb 6915
[2]Based upon the control at Day 1 after application of treatments
[3]Based upon the control at Day 10 after application of treatments From the results listed above in Table 3, it can be determined that a solution containing 2% caprylic acid significantly inhibits the growth of *Phytophthora infestans* on potato foliage. The treatment solution 2 was significantly different from the treatment 1 for disease control as determined via an ANOVA statistical test (P>0.95).

EXAMPLE 4

Inhibition of Fungus Infection on Strawberries

A field of strawberries (Northeaster variety) was partitioned into four separate areas and strawberries were harvested from each area. For each treatment group, berries were randomly selected from the four separate areas. Berries were submersed for 60 seconds in the specified treatment solution listed below in Table 4. After 60 seconds, the berries were removed from the solution, briefly drained, and incubated at room temperature on a screen suspended above water in a sealed chamber. The infected berries were analyzed to determine the host fungi. The primary host fungi were *Botrytis cinerea*, and the secondary fungi were *Rhizopus*. The results are listed below in Table 4.

TABLE 4

| Group | Treatment Solution | Infected berries (% of total) determined at The specified days after treatment (DAT) | | | | |
|---|---|---|---|---|---|---|
| | | Day 3 | Day 4 | Day 5 | Day 6 | Day 7 |
| 1. | Water | 70% | 85% | 100% | 100% | 100% |
| 2. | 0.35% glycolic acid | 75% | 90% | 100% | 100% | 100% |
| 3. | 0.35% glycolic acid and 0.35% caprylic/0.1% 6915[1]/0.05% mineral oil | 5% | 15% | 20% | 30% | 40% |
| 4. | 0.35% caprylic acid/0.1% 6915[2]/0.05% mineral oil | 25% | 50% | 60% | 65% | 75% |

[1]Cognis Emsorb 6915

It can be determined from analyzing the results listed above in Table 4 that caprylic acid (treatment #4) exhibits a significant inhibition of fungus infection. However, it is also determined that the combination of glycolic acid and caprylic acid (treatment #3) provide unexpected and synergistic inhibition of fungal infection of strawberries. No inhibition is found when only glycolic acid is used.

EXAMPLE 5
Inhibition of Fungus Infection on Strawberries

Strawberries described and treated as above in Example 4, with the solutions shown below in Table 5.

TABLE 5

| Group | Treatment Solutions | Infected berries (% of total) on days after treatment | | |
|---|---|---|---|---|
| | | Day 2 | Day 3 | Day 4 |
| 1. | Water | 75% | 90% | 100% |
| 2. | 0.35% glycolic acid | 70% | 95% | 100% |
| 3. | 0.35% glycolic acid + 0.70% caprylic acid/0.20% 6915[1]/0.10% mineral oil | 0% | 0% | 5% |

TABLE 5-continued

| Group | Treatment Solutions | Infected berries (% of total) on days after treatment | | |
|---|---|---|---|---|
| | | Day 2 | Day 3 | Day 4 |
| 4 | 0.70% caprylic acid/0.20% 6915[1]/0.10% mineral oil | 25% | 60% | 95% |

[1]Cognis Emsorb 6915

The data demonstrate the synergist fungicidal activity of caprylic and glycolic acids.

EXAMPLE 6

Inhibition of Fungal Infections on Strawberries: Comparison of Various Organic Acids as Synergists with Caprylic Acid Strawberries (Northeastern) were selected and treated as described above in Example 5 with the solutions listed below in Table 6. The predominant fungal infection was *Botrytis cinerea* and the secondary infection was *Rhizopus*.

TABLE 6

| Group | Treatment Solution | Infected berries (% of total treated berries): days after treatments | | | | |
|---|---|---|---|---|---|---|
| | | Day 2 | Day 3 | Day 5 | Day 7 | Day 9 |
| 1. | Water | 60% | 75% | 95% | 95% | 95% |
| 2. | 0.7% caprylic acid/0.2% 6915[1]/0.1% mineral oil | 5% | 25% | 55% | 75% | 80% |
| 3. | 0.7% caprylic acid/0.2% 6915[1]/0.1% mineral oil and 0.35% glycolic acid | 0% | 0% | 0% | 0% | 5% |
| 4. | 0.7% caprylic acid/0.2% 6915[1]/0.1% mineral oil and 0.35% potassium sorbate | 0% | 0% | 15% | 25% | 30% |

[1]Cognis Emsorb 6915

For Northeastern strawberries, glycolic acid in combination with caprylic acid exhibited unexpectedly high anti-fungal properties and was the best treatment under the test conditions.

EXAMPLE 7

Inhibition of Fungus Infections on Raspberries

Raspberries (Tulamen variety) harvested from four separate plots were divided into three groups, each group of harvested berries were submerged for 60 seconds in the appropriate solution listed below in Table 7, briefly drained and dried and then incubated at room temperature on a screen suspended above water in a sealed chamber. The predominant infection observed on the raspberries was *Botrytis cinerea* and the secondary infection was *Cladosporium*. The results are listed below in Table 7.

TABLE 7

| | | Infected berries (% of total) on days after treatment | | | |
|---|---|---|---|---|---|
| Group | Treatment Solution | Day 2 | Day 3 | Day 4 | Day 5 |
| 1. | Water | 61% | 85% | 96% | 96% |
| 2. | 0.7% caprylic acid/ 0.2% 6915[1]/0.1% mineral oil + 0.5% glycolic acid | 0% | 0% | 0% | 0% |
| 3. | 0.7% caprylic acid/ 0.12% oleic acid/0.01% Leciprime[2] | 0% | 0% | 0% | 0% |

[1] Cognis Emsorb 6915
[2] Leciprime N from Riceland

EXAMPLE 8

Inhibition of Fungal Growth by Caprylic Acid and Glycolic Acid

Potato dextrose agar (PDA) plates, +/− amendments (treatments #1-6, Table 8), were inoculated with *Septoria*, late blight or white mold. There were four replicate plates/treatment group/fungus type. After incubation of the plates at room temperature (three days), fungal growth was measured.

TABLE 8

| | | Measurement of fungal growth on day 2 or 3 after inoculum[4] | | | | | |
|---|---|---|---|---|---|---|---|
| | | Septoria | | Late blight | | White mold | |
| Group | Amendments in PDA Plates | Day 2 | Day 3 | Day 2 | Day 3 | Day 2 | Day 3 |
| 1. | 0.0175% C-8[1]/0.005% 6915/ 0.003% mineral oil | 92 | 94 | 82 | 93 | 24 | 52 |
| 2. | 0.0175% C-8[1]/0.005% 6915/ 0.003% mineral oil and 0.0175% glycolic acid | 60 | 69 | 65 | 78 | 41 | 65 |
| 3. | 0.07% C-8[1]/0.02% 6915[2]/0.01% mineral oil | 0 | 19 | 10 | 25 | 0 | 0 |
| 4. | 0.07% C-8[1]/0.02% 6915[2]/0.01% mineral oil and 0.0175% glycolic acid[3] | 0 | 2 | 0 | 10 | 0 | 0 |
| 5. | 0.0175% glycolic acid[3] | 80 | 90 | 79 | 104 | 127 | 108 |
| 6. | no amendments | 100 | 100 | 100 | 100 | 100 | 100 |

[1] C-8 stock solution: = 70% caprylic acid/20% 6915/10% mineral oil
[2] Cognis Emsorb 6915 (sorbitan monolaurate)
[3] Glycolic acid = DuPont 70% glycolic acid
[4] Based on fungal growth on the control plate (100%)
Addition of glycolic acid enhanced fungicidal activity of caprylic acid (C8).

EXAMPLE 9

Inhibitions of Fungal Infections on Fresh Raspberries

Raspberries (Heritage variety) were harvested from four plots. Nine berries per plot (4 plots) were used for each treatment group. The berries were randomly divided into six (6) groups. Each group of the harvested berries was submersed for 60 seconds in the appropriate solution listed below in Table 9. Thereafter the berries were removed from the solution, briefly drained and incubated at room temperature on a screen suspended above water in a sealed chamber. The predominant infection for the berries was determined to be *Botrytis cinerea*. The results are listed below in Table 9.

TABLE 9

| Group | Treatment Solution | Infected berries (% of total) on days after treatment | | | | | | |
|---|---|---|---|---|---|---|---|---|
| | | Day 2 | Day 3 | Day 4 | Day 6 | Day 8 | Day 10 | Day 12 |
| 1. | Water | 33% | 83% | 89% | 89% | 89% | 92% | 92% |
| 2. | 0.525% caprylic acid/0.15% 6915[1]/0.075% mineral oil | 0 | 0 | 11% | 17% | 44% | 67% | 67% |
| 3. | 0.75% tartaric acid | 31% | 58% | 86% | 92% | 92% | 92% | 92% |
| 4. | 0.525% caprylic acid/0.087% oleic acid/0.009% Leciprime[2] | 0 | 0 | 0 | 3% | 3% | 3% | 8% |
| 5. | 0.263% caprylic acid/0.044% oleic acid/0.005% Leciprime[2] | 0 | 0 | 0 | 6% | 14% | 25% | 33% |
| 6. | 0.131% caprylic acid/0.022% oleic acid/0.002% Leciprime[2] | 3% | 8% | 11% | 14% | 25% | 28% | 28% |

[1] Cognis Emsorb 6915 (sorbitan monolaurate)
[2] Leciprime N is a lecithin product from Riceland EXAMPLE 10
Inhibitions of Fungal Infections on Fresh Raspberries: Comparison of Various Fatty Acid Species (C6-C10) as Fungicide Active Ingredients Raspberries (Heritage variety) were harvested and treated as described above in Example 9. The results of the treatments for various saturated fatty acids are listed below in Table 10.

TABLE 10

| Group | Treatment Solutions | Infected berries (% of total) on days after treatment | | | | | |
|---|---|---|---|---|---|---|---|
| | | Day 1 | Day 2 | Day 3 | Day 5 | Day 7 | Day 9 | Day 11 |
| 1. | Water | 19% | 58% | 92% | 97% | 97% | 97% | 97% |
| 2. | 0.1% 6915[1]/0.05% mineral oil/0.35% caproic acid (C-6) | 3% | 39% | 75% | 97% | 97% | 97% | 100% |
| 3. | 0.1% 6915/0.05% mineral oil/0.35% heptanoic acid (C-7) | 0% | 0% | 6% | 44% | 69% | 83% | 89% |
| 4. | 0.1% 6915/0.05% mineral oil/0.35% caprylic acid (C-8) | 0% | 0% | 3% | 25% | 53% | 67% | 78% |
| 5. | 0.1% 6915/0.05% mineral oil/0.35% pelargonic acid (C-9) | 0% | 3% | 14% | 68% | 89% | 92% | 97% |
| 6. | 0.1% 6915/0.05% mineral oil/0.35% capric acid (C-10) | 0% | 31% | 69% | 97% | 100% | 100% | 100% |

[1] Cognis Emsorb 6915 (sorbitan monolaurate)

The above data indicate that the relative fungicidal activity of the fatty acid species against raspberry pathogens was: caprylic > heptanoic > pelargonic > capric > caproic acid.

EXAMPLE 11

Effects of Fungicide Formulation on Greenhouse Soybean Production

Five (5) groups of soybean plants (variety GL 2415) were grown to a height of 15-20 inches and then each group was treated with the indicated solutions listed below in Table 11. Each plant was treated with a solution at an application rate of 40 gpa at (40 psi). After treatment, the soybean plants were grown in a greenhouse for 31 days prior to harvest. The results of harvesting are listed below in Table 11.

TABLE 11

| | | Average production/plant[2] | | |
|---|---|---|---|---|
| Group | Treatment Solutions | Bean number | Total bean Weight (grams) | Weight (g) Per bean |
| 1. | Control (untreated) | 16.3 | 18.3 | 1.10 |
| 2. | 0.21% 6915[1] + 0.11% mineral oil | 22.8 | 25.7 | 1.13 |
| 3. | 0.21% 6915[1] + 0.11% mineral oil + 0.75% caprylic acid | 20.8 | 22.5 | 1.10 |
| 4. | 0.07% 6915[1] + 0.04% mineral oil + 0.25% caprylic acid | 21.0 | 24.2 | 1.14 |
| 5. | 0.02% 6915[1] + 0.01% mineral oil + 0.08% caprylic acid | 21.3 | 23.7 | 1.11 |

[1]Cognis Emsorb 6915
[2]Four repetitions (plants) per treatment group.

It can be seen from the data listed in Table 11 above that none of the caprylic acid (C8) treatments adversely affected soybean production. Moreover, there was no phytotoxicity (visual injury) from any of the caprylic acid treatments.

EXAMPLE 12

Efficacy of Selected C-8 or C-9 Formulations Containing amendment Tetrahydrofurfuryl salicylate and Huntsman PE 1198 Emulsifier as Inhibitors of Selected Fungal Pathogens Potato dextrose agar (PDA) plates, +/−amendments, were inoculated with selected pathogens. There were several replicate plates used per treatment group (per pathogen tested). After incubation of plates at room temperature, fungal growth was measured.

TABLE 12

| | % inhibition of selected pathogens[1] | | | | | | | | |
|---|---|---|---|---|---|---|---|---|---|
| | 0.015%, v/v of formulations | | | | | 0.100%, v/v of formulations | | | |
| Treatment Solutions | Late Blight | Alt | Botry | Pyth U. | White Mold | Pestal | Collet | C. paras. | A. Paras. |
| 1 = 85% pelargonic acid 15% Huntsman PE1198 | 15 | 49 | 30 | 27 | 76 | 85 | 52 | 44 | 66 |
| 2 = 85% pelargonic acid 7% Huntsman PE 1198 8% tetrahydrofurfuryl salicylate | 27 | 42 | 21 | 33 | 53 | 79 | 41 | 45 | 48 |
| 3 = 70% caprylic acid 10% Huntsman PE 1198 20% tetrahydrofurfuryl salicylate | 31 | 44 | 42 | 26 | 58 | 88 | 48 | 50 | 50 |
| 4 = 70% pelargonic acid 10% Huntsman PE 1198 20% tetrahydrofurfuryl salicylate | 23 | 41 | 21 | 32 | 52 | 86 | 47 | 59 | 39 |
| 5 = 55% pelargonic acid | 49 | 44 | 20 | 42 | 39 | 84 | 46 | 68 | 74 |

TABLE 12-continued

| | % inhibition of selected pathogens[1] | | | | | | | | |
|---|---|---|---|---|---|---|---|---|---|
| | 0.015%, v/v of formulations | | | | | 0.100%, v/v of formulations | | | |
| Treatment Solutions | Late Blight | Alt | Botry | Pyth U. | White Mold | Pestal | Collet | C. paras. | A. Paras. |
| 10% Huntsman PE 1198 35% tetrahydrofurfuryl salicylate | | | | | | | | | |
| 6 = 40% pelargonic acid 10% Huntsman PE 1198 50% tetrahydrofurfuryl salicylate | 77 | 45 | 19 | 44 | 29 | 79 | 53 | 66 | 72 |

[1]% inhibition relative to control plates (fungal inoculum without any treatment solution)
Late blight = *Phytophthora*
Alt—*Alternaria* (SWREC)
Botry = *Botrytis cinerea* (SWREC)
Pyth. U. = *Pythium ultimum*
Pestal = *Pestalotia infestans*
Collet = *Colletotrichia* (SWREC)
C. para = *Cylindrocladium parasiticus*
A. paras. = *Apergillus parasiticus*
The average percent inhibition of all pathogens
Treatment 1 = 47.7%
Treatment 2 = 54.6%
Treatment 3 = 56.6%
Treatment 4 = 51.7%
Treatment 5 = 46.8%
Treatment 6 = 51.8%

Overall, the combination of tetrahydrofurfuryl salicylate and pelargonic acid (treatments 2-6) exceeded the fungicidal activity of pelargonic acid, alone, (treatment 1) for certain pathogens.

EXAMPLE 13

Synergism Between Caprylic Acid and Organic Acids: Inhibition of *Botrytis cinerea* and White Mold Potato dextrose agar (PDA) plates, +/−amendments, were inoculated with selected pathogens. There were several replicate plates used per treatment group (per pathogen tested). After incubation of plates at room temperature, fungal growth was measured.

TABLE 13

| Treatment* | Inhibition (%) of Botrytis cinerea | Inhibition (%) of white mold |
|---|---|---|
| 1 0.014% caprylic acid | 88 | 34 |
| 2 0.014% caprylic acid + 0.010% glycolic acid | 98 | 71 |
| 3 0.014% caprylic acid + 0.010% diethylamine salicylate | 99 | 93 |
| 4 0.010% citric acid | 0 | 0 |
| 5 0.010% succinic acid | 0 | 0 |
| 6 0.010% glycolic acid | 0 | 0 |
| 7 0.010% diethylamine salicylate | 0 | 7 |

Synergy between caprylic acid and each organic acid for white mold
Synergy between caprylic acid and each organic acid for Botrytis

*Treatment formulation: 70% C-8/20% Emsorb 6915/10% mineral oil: 0.020%, v/v, of formulation = 0.0140% C-8 in potato dextrose agar plate Combinations of caprylic acid (C8) with organic acids for both pathogens were synergistic.

EXAMPLE 14

Comparison of Low and High Rates of Caprylic Acid Applied to Berry and Potato Plant Foliage: Inhibition of *Botrytis cinerea*

The foliage of strawberry plants (Honeoye variety) and potato plants (Snowden variety) were inoculated with fresh *B. cinerea* and incubated at room temperature at 100% humidity for 2-3 days. The inoculated foliage of the plants was then treated with the treatment solutions listed in Table 14 below. It should be noted that no phytotoxicity was observed in any of the treatment solutions.

TABLE 14

| Treatment Solutions | Inhibition (%) of Botrytis on Potato Foliage | Inhibition (%) of Botrytis on Strawberry Foliage |
|---|---|---|
| 1 Water | 0 | 0 |
| 2 0.08% caprylic acid formulation | 15 | 62 |
| 3 0.08 caprylic acid formulation + 0.02% glycolic acid | 46 | 53 |
| 4 1.5% caprylic acid formulation | 20 | 61 |
| 5 1.5% caprylic acid formulation + 0.02% glycolic acid | 46 | 52 |

Caprylic acid formulation: 70% caprylic acid/20% Cognis Emsorb 6900/10% mineral oil
Glycolic acid (70%) from DuPont
Actual caprylic acid concentration in treatment #2, 3 was 0.056%
Actual caprylic acid concentration in treatment #4, 5 was 1.050%
Application of treatments at 20 gallons/acre (25 psi)
Foliage inoculated with fresh B. cinerea and incubated at room temperature in moisture chambers for 2-3 days
Strawberry and potato varieties were Honeoye and Snowden, respectively.

No phytotoxicity observed

The data indicate that a lower application rate of formulation containing caprylic acid (C8, 0.08%) exhibited a similar fungicidal activity as a higher application rate of the caprylic acid (C8 at 1.5%). Further, formulations containing glycolic acid exhibited enhanced fungicidal activity on potato foliage than similar formulation without the addition of the glycolic acid.

EXAMPLE 15

Inhibition of White Mold on Vista Dry Bean Foliage: Caprylic Acid Formulations Containing Different Adjuvants Experimental details given below in Table 15 illustrate that the addition of tetrahydrofurfuryl salicylate enhanced the fungicidal activity of formulations containing caprylic acid (C8) against white mold.

TABLE 15

| Treatment Solutions* | Percent Inhibition of White Mold |
|---|---|
| Water, control | 0 |
| 70% caprylic acid/20% Cognis 6915/10% mineral oil | 61 |
| 51% caprylic acid/39% Cognis 6915/10% high fructose corn syrup | 60 |
| 47% caprylic acid/36% Cognis 6915/17% tetrahydrofurfuryl salicylate | 92 |
| 55% caprylic acid/41% Cognis 6915/4% Exacto 390 | 50 |

*Same amount (0.42%) of caprylic acid used in all treatments

All formulations, as concentrated emulsions or diluted in water, were stable; i.e., no phase separation was observed after storage of emulsions for several days. Twelve leaves/treatment group, after treatment, inoculated with white mold from PDA plates. Leaves incubated at 100% humidity for 2 days and zones of infection measured.

No phytotoxicity observed for any of the treatments.

EXAMPLE 16

Inhibition of Rhizoctonia solani on Cotton Foliage

The combination of caprylic acid (C8) and tetrahydrofurfuryl salicylate with an emulsifier, PE 1198, was highly effective against R. solani.

TABLE 16

| Treatment Solution | Application Rate* | Percent Inhibition of R. solani |
|---|---|---|
| Water, control | | 0 |
| 70% caprylic acid/20% PE 1198/10% tetrahydrofurfuryl salicylate | 0.1%, v/v | 89 |
| 70% caprylic acid/20% PE 1198/10% tetrahydrofurfuryl salicylate | 0.2%, v/v | 94 |

*0.1 or 0.2%, v/v, formulation, in water
Foliage dipped in treatment, drained, dried, and inoculated with fresh culture of Rhizoctonia solani from PDA plate.
Four leaves from each plant/treatment group inoculated and incubated at 100% humidity for 7 days.
PE 1198 emulsifier from Huntsman

EXAMPLE 17

Comparison of Caprylic Acid and Pelargonic acid as Active Ingredients in Fungicides and Comparison of Emulsifiers Potato dextrose agar (PDA) plates, +/−amendments, were inoculated with selected pathogens. There were several replicate plates used per treatment group (per pathogen tested). After incubation of plates at room temperature, fungal growth was measured.

TABLE 17

| | % Inhibition of Selected Pathogens by Formulations | | | | | | | |
|---|---|---|---|---|---|---|---|---|
| Treatment Solutions* | C. para. | Alt | Late Blight | S. Minor | Pyth. U. | Botr | White Mold | Avg |
| 1 85% caprylic acid/15% PE 1198 | 7 | 33 | 14 | 83 | 12 | 30 | 68 | 35 |
| 2 85% pelargonic acid/15% PE 1198 | 7 | 31 | 25 | 84 | 20 | 25 | 80 | 39 |
| 3 85% caprylic acid/15% 6915 | 1 | 11 | 0 | 66 | 7 | 17 | 65 | 24 |

TABLE 17-continued

% Inhibition of Selected Pathogens by Formulations

| Treatment Solutions* | C. para. | Alt | Late Blight | S. Minor | Pyth. U. | Botr | White Mold | Avg |
|---|---|---|---|---|---|---|---|---|
| 4 85% pelargonic acid/15% 6915 | 1 | 12 | 0 | 78 | 17 | 13 | 76 | 28 |
| 5 85% caprylic acid/15% 6900 | 0 | 10 | 0 | 75 | 5 | 20 | 53 | 23 |
| 6 85% caprylic acid/15% 6964 | 0 | 22 | 8 | 85 | 9 | 40 | 65 | 33 |

*0.015%, v/v, formulation used (actual C8 or C9 used was 0.013%)
C. para = Cylindrocladium parasiticus
Alt = Alternaria
Late blight = Phytophtora infestans
S. minor = Sclerotinia minor
Pyth. U. = Pythium ultimum
Botr = Botrytis cinerea
White mold = Sclerotinia sclerotiorum The data listed in Table 17 above indicate that pelargonic acid under these experimental conditions, exhibited slightly better or same fungicidal activity as caprylic acid against a wide variety of fungi (PDA plate assay). Further the emulsifier, PE 1198, provided better results than other emulsifiers.

EXAMPLE 18

Comparison of Caprylic Acid (C8) and Pelargonic Acid (C9)+/−Stoichiometric Amounts of Organic Acid Amendments Potato dextrose agar (PDA) plates, +/−amendments, were inoculated with selected pathogens as listed below in Table 18. There were several replicate plates used per treatment group (per pathogen tested). After incubation of plates at room temperature, fungal growth was measured.

TABLE 18

% Inhibition by C8 (C9) +/− Organic Acid

| Treatment Solution* | Late Blight | | Alternaria | | Botrytis | | Pyth U. | | White Mold | |
|---|---|---|---|---|---|---|---|---|---|---|
| | C8 | C9 | C8 | C9 | C8 | C9 | C8 | C9 | C8 | C9 |
| C8 or C9 | 85 | 61 | 48 | 41 | 57 | 39 | 57 | 48 | 96 | 93 |
| + glycolic acid 100% | 98 | 96 | 62 | 56 | 78 | 78 | 100 | 74 | 96 | 97 |
| + glycolic acid, 70% (tech) | 99 | 91 | 62 | 59 | 86 | 76 | 100 | 74 | 96 | 97 |
| + gluconic acid | 91 | 90 | 45 | 53 | 90 | 43 | 94 | 61 | 87 | 83 |

*The treatment solution was added to PDA C8, caprylic acid, and C9, pelargonic acid, at 0.025% in PDA (potato dextrose agar) plates Organic acids at 0.013% in PDA (acids at same dry wt. basis) Both C8 and C9: 85% C8 or C9/15% 6915 (concentrated emulsions used in PDA)
The data above indicate that overall, caprylic acid (C8) (+/− organic acids) exhibited greater fungicidal activity than pelargonic acid (C9) (+/− organic acids).

Herbicidal Compositions and Methods for their use A "ready-to-use formulation" of the agricultural composition (a concentrated formulation that is diluted in water or other diluent such as seed oil, ethanol, etc.) having herbicidal properties can include the organic acid species together with one or more fatty acid(s) in an amount sufficient to induce desiccation and/or death of a treated plant. In preferred embodiments, a ready-to-use herbicide formulation for use in the present invention comprises at least about 50% v/v, of fatty and organic acids; more preferably at least about 25% v/v; and still yet more preferably at least about 5% % v/v of the fatty acid and organic acid, based upon the total volume of the formulation.

The pesticidal compositions having herbicidal properties include a fatty acid, or a salt thereof having between 5 and 22 carbon atoms included in a herbicidally effective amount; an organic carboxylic acid, or a salt thereof, different from the fatty acid, and an emulsifier. Preferred fatty acids include, but are not limited to hexanoic acid, heptanoic acid, octanoic acid, nonanoic acid, decanoic acid and mixtures thereof. Preferred organic acids include but are not limited to glycolic acid, propionic acid, lactic acid, succinic acid salicylic acid, and other salts of salts of salicylic acid, citric acid, tartaric acid and mixtures thereof. Preferred emulsifiers include, but are not limited to phosphate esters, sorbitan esters, lecithins and combinations thereof. Preferred herbicides further include an additive selected from the group consisting of an adjuvant, a diluent, and a combination thereof.

The agricultural composition having herbicidal properties can include both the fatty acids species and the organic acid species, different from the fatty acid species in a wide range of ratios. In preferred embodiments, the ratio of fatty acid species to organic acids species is in a weight ratio of between 1:1000 to about 1000:1. More preferably, the weight ratio of fatty acid species to organic acid species is between about 1:5 to about 5:1. The agricultural composition for use in the present invention can be prepared by admixing all desired ingredients at the same time. The application of the compositions described herein, at rates ranging from about 0.10 to about 1000 pounds per acre are preferred. Applications involving the compositions derived from a concentrate of the compositions described herein diluted with a carrier are similarly preferred. The application of such compositions diluted with water include a concentrate comprising from about 10% to about 95% of the diluted composition on a volume/volume basis.

As with the fungicidal compositions, the fatty acid species can be premixed with one or more additives such as adjuvants, surfactants, other emulsifiers, and/or diluents in water. When premixed, the ratio of fatty acid to additive(s) can be between about 1:5 to about 1000:1. The fatty acid, emulsifier and additive(s), either singly or as a combined pre-mix, can be suitably dissolved in a solvent such as water, alcohol, and/or an organic solvent, such as an oil or ketone, suitable for treatment of agricultural products or plants.

In preferred embodiments, either the concentrate or the ready-to-use formulation is admixed with a variety of additives; for example, adjuvants, surfactants, emulsifiers, and/or diluents. The additive can be selected from a wide variety of known commercially available products. Typical adjuvants, surfactants, and/or emulsifiers for use with fatty acids include any synthetic or natural emulsifier including for example: alkanolamides, alkoxylated triglycerides, alkyl benzene sulfonates, alkyl phenol ethoxylates, alkyl polyglycosides, anionic-nonionic mixtures, EO-PO block polymers, ethoxylated fatty alcohols, ethoxylated fatty amines, ethoxylated tristyrylphenols, fatty acid PEG esters, fatty alcohol ether sulfates, lecithins, naphthalene sulfonate condensates, phosphate esters, polyol esters, quaternary derivatives, sorbitan esters, and combinations thereof. Preferred emulsifiers includes phosphate esters and particularly preferred phosphate esters include lecithins, Huntsman Chemical PE 1168, 1248, 2258, 2188, 1198 and BASF Klearfac AA270. Although a variety of diluents can be utilized, preferred diluents include, but are not limited to kerosene, xylene, mineral oil, vegetable or seed oil, alcohol and a mixture thereof.

In selected embodiments, a "ready-to-use formulation" (i.e., a concentrated formulation diluted in water or other solvent) according to the present invention contains between about 1% v/v and about 90% v/v fatty acid, more preferably between about 10% v/v and about 50% v/v of the fatty acid, still more preferably between about 2% v/v and about 10% v/v of the fatty acid. The organic acid is included in an amount between about 1% v/v and about 90% v/v; more preferably, between about 1% v/v and about 10% v/v (or wt/vol, for solid organic acids). When used as a foliar spray application treatment, the herbicide/desiccant composition can be directly applied to the unwanted plants or crop products in the case of a desiccant. Furthermore, in use, the herbicide composition can be applied as a single use or single treatment, or in multiple treatments.

In other embodiments, the herbicide/desiccant composition can be combined with one or more other treatment processes and compositions. For example, the herbicide/desiccant composition can be combined with a fungicide composition or an insecticide composition. A combination of the herbicide/desiccant with one or more other treatment compositions and applications obviously reduces treatment costs and consequently can improve efficiency of operation.

In preferred embodiments, the selected combination of a fatty acid species and an organic acid species exhibits unexpected results or synergism by providing improved herbicidal/desiccant activity over any of the individual components by themselves. The organic acid, alone, has little or no herbicidal activity; however, when combined with the fatty acid, a strong synergism results. Similarly, the use of specific emulsifiers can provide an additional enhancement of herbicidal/desiccant activity.

The compositions according to the present invention can be used to kill/desiccate a variety of grasses, broadleaves, and crop plants. Grasses killed or desiccated include, but are not limited to is barnyard grass, bluegrass, buffalograss, crabgrass, fall panicum, fescue, foxtail, goosegrass, johnsongrass, nutsedge, oatgrass, orchardgrass, quackgrass, ryegrass, wildproso millet, witchgrass, and combinations thereof. Broadleaf plants killed or desiccated by the herbicidal compositions include, but are not limited to, black medic, broadleaf plantain, buckhorn plantain, bull thistle, chicory, chickweed, common burdock, common cocklebur, common ivy, common lambsquarter, common mallow, common purslane, clover, dandelion, Eastern black nightshade, horsenettle, horseweed, jimsonweed, ladysthumb, milkweed, Pennsylvania smartweed, poison ivy, prickly lettuce, prickly sida, ragweed, redroot pigweed, sheperd's-purse, sunflower, velvetleaf, wild buckweed, wild carrot, wild mustard, yellow rocket, and combinations thereof. Crop plants which can be desiccated include, but are not limited to, canola, cotton, dry bean, dry pea, onion, potato, seed alfalfa, seed grass, soybean, sugarcane and tomato.

The herbicide/desiccant composition can be provided to the end user either as a liquid concentrate or in a "ready-to-use composition" (i.e., a concentrated formulation diluted in water or other diluent). When provided as a liquid concentrate, the herbicide/desiccant composition includes the fatty acid species in a range, of between about 30% v/v and about 99.5% v/v, the organic acid species in a range between about 1% v/v and about 50% v/v, and the emulsifier(s) in a range between about 0.5% v/v and about 70% v/v.

For the purpose of promoting further understanding and appreciation of the present invention and its advantages, the following examples directed to herbicidal/desiccant compositions and methods for their use are provided. It will be understood, however, that these examples are illustrative and not limiting in any fashion. Unless specifically indicated to the contrary, all percentages listed below in the following examples are percentage by volume, based upon the total volume of the resulting composition.

EXAMPLE 19

Comparison of Emulsifiers used in Herbicide Formulations Containing Pelargonic Acid (C-9) in Replicate Field Trials (2) with Mixed Weed Species The herbicidal/desiccant activity of experimental formulations and a commercial pelargonic acid-based product (Scythe, Dow AgroScience) were compared at a field test site with multiple replications of each treatment in a randomized complete block design. Common grass and broadleaf weed species at 6 to 11 inches were used. Plot size was 3 by 6 ft with the experiments repeated over time. A single application of treatments was made at 563 L/ha at 276 kPa (60 gallons per acre at 45 pounds per square inch or psi) to plants using a calibrated backpack sprayer. Ratings of plant injury (0 to 100%) were made at the indicated days after treatments. Data were subjected to analysis of variance and mean separation for least significant difference (LSD) at the 0.05 level. A phosphate ester (PE 1198), when formulated with a fatty acid, was shown to be superior to other emulsifier types when the emulsified formulation is used as an herbicide (Table 19). Moreover, the pelargonic acid/PE 1198 formulation is significantly better than the commercial herbicide Scythe, similarly containing pelargonic acid.

TABLE 19

| Treatment* | Plant Injury** | LSD (0.05)*** |
|---|---|---|
| Scythe | 41 | B |
| 70% C9/20% Emsorb 6900/10% mineral oil | 45 | B |
| 70% C9/20% Emsorb 6915/10% mineral oil | 49 | B |
| 70% C9/20% PE 1198/10% mineral oil | 64 | A |
| Control (no treatment) | 0 | |

*2.5%, v/v formulation diluted in water
**Average injury rating (2 trials), where injury scale was 0-100% and ratings for both trials at 1 day after treatment
***Least Significant Difference Test where P was 0.05 and means within column with similar letters are not significantly different at 5% level.
EMSORB was formerly a registered trademark of National Distillers and Chemical Corporation, 99 Park Avenue, New York, NY 10016.

EXAMPLE 20

Comparison of Several Commercial Phosphate Esters as Emulsifiers in Herbicide Formulations Containing Pelargonic Acid (C9), Lactic Acid and Oleic Acid Seed of weed species noted below were planted in BACCTO professional potting mix (Michigan Peat Co., P.O. Box 980129, Houston, Tex. 77089) in separate 900-ml plastic pots. The plants were grown in a greenhouse at 25+/−2 C with supplemental sodium vapor lights providing a noon time intensity of 1,000 μmol m$^{-2}$s$^{1}$ photon flux with a 16 h day/8 h night. The plants were watered and fertilized with a 20-20-20: NPK solution as needed.

Experimental treatments, as described in Table 20 were applied as foliar applications to described weed species. At time of treatments, weed species were at three to six inches in height. A single application of treatments was made at 376 L/ha at 276 kPa (40 gallons per acre at 25 psi) to plants using a calibrated track sprayer.

Herbicidal activity/desiccation or plant injury ratings (0 to 100% injury) were made at indicated days after treatment (DAT). Although herbicidal/desiccant activity was rapid and generally reached a maximum at 1 DAT, results could be variable due to sunlight, temperature, and formulation type. Therefore, in general, results were averaged over two ratings over two days after treatments. Trials were repeated and all treatments had multiple replications depending on the experiment. A completely randomized design was used. All data were subjected to analysis of variance and mean separation for least significant difference (LSD) at the 0.05 level. Herbicidal properties of pelargonic acid formulations emulsified with various phosphate ester products (Huntsman Chemical) 20 proved similar (Table 20).

TABLE 20

| Treatments | Average rating (0 to 100% plant injury)** | | | Average Rating |
|---|---|---|---|---|
| (1.5%, v/v, in water)* | Velvetleaf | Chickweed | Giant foxtail | |
| PE 1198, as emulsifier | 47 | 43 | 46 | 46 |
| PE 1168, as emulsifier | 49 | 45 | 45 | 47 |
| PE 1248, as emulsifier | 48 | 44 | 45 | 46 |
| PE 2258, as emulsifier | 49 | 43 | 45 | 46 |
| PE 2188, as emulsifier | 42 | 41 | 44 | 42 |

*Each treatment contained 70% C9/10% L-lactic/10% oleic acid/10% emulsifier
**Average rating based on two evaluations (day 1 and 2 after application of treatments)

EXAMPLE 21

Comparison of Emulsifiers used with C9+/−L-Lactic Acid: as Enhanced Herbicides for Velvetleaf and Giant Foxtail Velvetleaf and giant foxtail were grown in the greenhouse and treated to evaluate the herbicide formulations shown in Table 21 according to the procedures described in Example 20, above. A relatively low application rate (1.25%, v/v) of herbicide formulations was used to properly distinguish treatment effects and relative potency of formulations. The greatest herbicidal effect for velvetleaf and giant foxtail was achieved from pelargonic acid emulsified with a phosphate ester (Table 21). Pelargonic acid emulsified with sorbitan monolaurate (Cognis 6915) was not as effective. Cognis is a registered trademark of Cognis Deutschland GmbH CORPORATION FED REP GERMANY, Henkelstrasse 67 D-40191 Duesseldorf FED REP GERMANY.

TABLE 21

| | Plant injury (0-100%), days after treatment | |
|---|---|---|
| Treatments | Day 1 | Day 2 |
| Velvetleaf (10-14 inches) | | |
| 85% C9/15% Huntsman PE 1198 | 18 | 24 |
| 85% C9/15% BASF Klearfac AA270 | 20 | 32 |
| 85% C9/15% Cognis 6915 | 14 | 20 |
| 85% C9/5% PE 1198/10% L-lactic acid (88%) | 14 | 33 |
| Giant foxtail (20-26 inches) | | |
| 85% C9/15% Huntsman PE 1198 | 36 | 51 |
| 85% C9/15% BASF Klearfac AA270 | 46 | 57 |
| 85% C9/15% Cognis 6915 | 37 | 48 |
| 85% C9/5% PE 1198/10% L-lactic acid (88%) | 46 | 54 |

1.25%, v/v of each formulation used in water, for single applications of treatments at 40 gallons/acre (25 psi)

EXAMPLE 22

The Importance of Emulsifier Type in Determining Herbicidal Performance with Grasses and Broadleaves The method described in Example 20 was used for growing seeds of lambsquarter, velvetleaf, giant foxtail and barnyard grass in Baccto potting soil and for treating plants with herbicide candidates. The specific herbicide candidates included pelargonic acid (C-9)/glycolic acid formulations comparing a phosphate ester (PE 1198) and with other types of emulsifiers. The results are provided below in Table 22. For both grasses (giant foxtail, barnyard grass) and broadleaf weed species (common lambsquarter, velvetleaf), the C-9 formulations including the phosphate emulsifier, PE 1198, demonstrated the greatest herbicidal activity compared to C-9 formulations containing other non-phosphate ester emulsifiers.

TABLE 22

| Treatments* | Plant Injury (0-100%)** |
|---|---|
| Common Lambsquarter (6-11 inches) | |
| 70% C9/10% mineral oil/20% Cognis 6900 | 50 |
| 70% C9/10% mineral oil/20% Cognis 6915 | 56 |
| 70% C9/10% mineral oil/20% Cognis 6964 | 48 |
| 70% C9/10% mineral oil/20% PE 1198 | 60 |
| Velvetleaf (7-11 inches) | |
| 70% C9/10% mineral oil/20% Cognis 6900 | 58 |
| 70% C9/10% mineral oil/20% Cognis 6915 | 56 |
| 70% C9/10% mineral oil/20% Cognis 6964 | 56 |
| 70% C9/10% mineral oil/20% PE 1198 | 64 |
| Giant foxtail (12-14 inches) | |
| 70% C9/10% mineral oil/20% Cognis 6900 | 54 |
| 70% C9/10% mineral oil/20% Cognis 6915 | 57 |
| 70% C9/10% mineral oil/20% Cognis 6964 | 46 |
| 70% C9/10% mineral oil/20% PE 1198 | 66 |
| Barnyard grass (19-22 inches) | |
| 70% C9/10% mineral oil/20% Cognis 6900 | 55 |
| 70% C9/10% mineral oil/20% Cognis 6915 | 59 |

TABLE 22-continued

| Treatments* | Plant Injury (0-100%)** |
|---|---|
| 70% C9/10% mineral oil/20% Cognis 6964 | 57 |
| 70% C9/10% mineral oil/20% PE 1198 | 62 |

*Each treatment contained 1%, v/v glycolic acid and 2%, v/v of fatty acid formulation, all added to water.
**Average of two ratings (day 1 and day 2)
Single application of treatments at 40 gallons/acre (25 psi)
Six replicates/treatment

EXAMPLE 23

Comparison of Commercial Herbicide Scythe and Experimental Formulations Containing (C-9+/−Lactic or Glycolic) Emulsified with PE 1198

Herbicidal/desiccant activity of experimental formulations described below in Table 23 and a commercial pelargonic acid-based product (Scythe, Dow AgroScience) were compared at a field test site with multiple replications of each treatment in a randomized complete block design. Other trial parameters utilized, including analysis of ratings, are described in Example 20. The C-9/PE 1198 formulation proved considerably more effective than Scythe, and the addition of lactic or glycolic to C-9/PE 1198 further improved the herbicidal activity of the C-9 formulation.

TABLE 23

| | Average ratings (plant injury, 0-100%) at selected days after treatment | | |
|---|---|---|---|
| Treatments (v/v) | 1 | 3 | 5 |
| 3% Scythe | 37 | 51 | 54 |
| 3% C | 50 | 69 | 69 |
| 3% C/LA | 57 | 71 | 75 |
| 3% C/GA | 57 | 71 | 74 |
| 5% Scythe | 58 | 81 | 82 |
| 5% C/LA | 75 | 90 | 86 |

C = 85% C9/15% PE 1198
C/LA = 85% C9/5% PE 1198/10% L-Lactic acid (88%)
C/GA = 80% C9/10% PE 1198/10% glycolic acid (70%)
Single application at 60 gallons/acre (45 psi), eight replicates/treatment group
Weed species: grasses, red and white clover, dandelion and buckhorn plantain

EXAMPLE 24

Comparison of Commercial Herbicide Scythe with Experimental Formulations with Velvetleaf Seeds of velvetleaf were grown and herbicide evaluations are described in Example 20. A comparison of Scythe (Dow AgroScience) as a non-selective herbicide and pelargonic acid formulations emulsified with a phosphate ester (PE 1198) are shown below in Table 24. The experimental formulation based on C9/PE 1198/oleic/lactic with or without glycolic acid proved superior to Scythe.

TABLE 24

| Treatments (2%, v/v)* | Rating (0-100% plant injury) at one day after application of treatments 1 |
|---|---|
| Scythe | 40 |
| 60% C9/10% PE 1198/15% oleic acid/15% L-lactic acid | 56 |
| 60% C9/10% PE 1198/15% oleic acid/15% L-lactic acid + 70% glycolic acid | 56 |
| Control (untreated plants) | 0 |

*2%, v/v, of C9/1198/oleic/lactic acid formulation +/−2% glycolic acid
Single application at 40 gallons/acre (25 psi) with four replications/treatment group

EXAMPLE 25
Succinate Enhancement of C9+Klearfac AA270 as a Desiccant for Dry Beans The methods described in Example 20 were utilized for growing two classes of dry bean (midnight and vista) in a greenhouse and for evaluating experimental formulations as desiccants. However, in this example, the injury to dry bean foliage and stems was evaluated, in lieu of a herbicidal effect on weed species. Efficacy of both the acid and salt forms of succinate, as synergists for pelargonic acid-based formulations (emulsified with a phosphate ester), is provided below in Table 25.

TABLE 25

| | Plant injury (average rating*) Dry Bean Class | |
|---|---|---|
| Treatments | Midnight | Vista |
| 0.7% MS 25 (v/v) | 34 (100%) | 42 (100%) |
| 0.7% MS 25 + 0.1% diammonium succinate (g/v) | 39 (115%) | 44 (105%) |
| 0.7% MS 25 + 0.25% diammonium succinate (g/v) | 40 (118%) | 55 (131%) |
| 0.7% MS 25 + 0.1% succinic acid (g/v) | 50 (147%) | 45 (107%) |
| 0.7% MS 25 + 0.25% succinic acid (g/v) | 56 (164%) | 69 (164%) |
| control (untreated) | 0 | 0 |

*Average rating based on 0-100% plant injury (foliage and stems)
MS 25: 85% C9/15% BASF Klearfac AA270
Single application of treatments at 40 gallons/acre (25 psi)
Multiple replications per treatment group

EXAMPLE 26
Desiccant Property Enhancement of C9+PE 1198 by the Addition of L-lactic Acid and its Superiority over Commercial Product The performance of the C-9 formulations emulsified with a phosphate ester as crop harvest aids and a comparison of this performance with that of Scythe (Dow AgroScience) are shown in Table 26. Growth of three classes of dry bean (pinto, black and navy) in field soil, general field trial design and plant injury ratings are described. Application of treatments was made at physiological maturity; i.e., at $1^{st}$ sign of foliage yellowing. Treatment plots were 50 foot, 4-row plots, with 2 middle rows evaluated for plant injury. As noted in Table 26, C-9/PE 1198 was substantially more effective as a crop desiccant than Scythe. The addition of L-lactic acid to the C-9/PE 1198 formulation provided a further marked improvement in performance.

TABLE 26

| Treatment | RATINGS FOR VINE, FOLIAGE AND POD DESICCATION (PERCENT INJURY) | | | | | | | | |
|---|---|---|---|---|---|---|---|---|---|
| A, B, or C | Pinto dry Beans | | | Navy dry Beans | | | Black dry Beans | | |
| formulation, v/v | VINE | FOLIAGE | PODS | VINE | FOLIAGE | PODS | VINE | FOLIAGE | PODS |
| 3%, A | 85 | 95 | 84 | 69 | 65 + 75 | 66 | 83 | 80 + 95 | 76 |
| 3%, B | 90 | 95 | 84 | 80 | 75 + 85 | 71 | 86 | 80 + 95 | 75 |
| 3%, C | 65 | 75 | 63 | 66 | 60 + 75 | 63 | 72 | 50 + 75 | 61 |
| 5%, A | 90 | 93 | 83 | 85 | 80 + 90 | 77 | 82 | 80 + 93 | 76 |
| 5%, B | 93 | 99 | 88 | 82 | 90 + 95 | 85 | 87 | 90 + 99 | 78 |
| 6%, A | 92 | 95 | 85 | 90 | 85 + 95 | 81 | 85 | 83 + 95 | 77 |
| 6%, B | 94 | 99 | 85 | 90 | 90 + 95 | 86 | 87 | 90 + 98 | 80 |
| Control (untreated) | 44 | 50 | 45 | 4 | 5 | 5 | 5 | 5 | 5 |

A = 85% C9/15% PE1198
B = 85% C9/5% PE 1198/10% L-lactic acid (88%)
C = Scythe (Dow AgroScience
C9 (pelargonic acid)
PE 1198, a phosphate ester emulsifier from Huntsman Chemical EXAMPLE 27
Field Trials for the Desiccation of Soybean (DeKalb 2351) Demonstrating Desiccation Enhancement by the Combination of C9/PE 1198 with Organic Acid (Lactic, Succinic)

The effect of organic acid synergists on fatty acid formulations, emulsified with a phosphate ester, as a harvest aid for soybean was studied and the results provided in Table 27, below. Varying application rates (1.25 to 2.00%, v/v) and amounts (20 and 40 gallons/acre) of applied treatments are compared. Concentrated fatty acid formulations and the synergist L-lactic acid, each at v/v, and succinic acid (g/v), as a synergist, were thoroughly mixed into water and then applied as foliar sprays. A single application of treatments using a calibrated backpack sprayer was made at physiological maturity; i.e., at $1^{st}$ sign of foliage yellowing. Ratings of plant injury (0 to 100%) were made several days after treatment applications.

TABLE 27

| Trial | Application Rates | Treatments | 1 | 2 | 3 | 4 | 5 | 7 | Average |
|---|---|---|---|---|---|---|---|---|---|
| 1 | (1.25%, v/v) at 40 gpa | 85% C9/15% Emulsifier B | 39 | 44 | 55 | 63 | 71 | 67 | 57 |
| | | 85% C9/5% Emulsifier B/10% L-lactic acid (88%) | 70 | 60 | 70 | 76 | 83 | 75 | 70 |
| | | 85% C9/10% Emulsifier B/5% L-lactic acid (88%) | 55 | 60 | 73 | 83 | 83 | 71 | 71 |
| 1 | (1.25%, v/v) at 20 gpa | 85% C9/15% Emulsifier B | 14 | 6 | 8 | 18 | 23 | 29 | 16 |
| | | 85% C9/5% Emulsifier B/10% L-lactic acid (88%) | 24 | 19 | 21 | 26 | 33 | 35 | 26 |
| | | 85% C9/10% Emulsifier B/5% L-lactic acid (88%) | 31 | 26 | 34 | 43 | 53 | 60 | 41 |
| 2 | (2.00%, v/v) at 40 gpa | 85% C9/15% Emulsifier B | 79 | 85 | 87 | 90 | 91 | | 86 |
| | | 85% C9/5% Emulsifier B/10% L-lactic acid (88%) | 81 | 88 | 89 | 90 | 89 | | 87 |
| | | 85% C9/10% Emulsifier B/5% L-lactic acid (88%) | 80 | 86 | 92 | 91 | 92 | | 88 |
| 2 | (2.00%, v/v) at 20 gpa | 85% C9/15% Emulsifier B | 46 | 58 | 66 | 61 | 74 | | 61 |
| | | 85% C9/5% Emulsifier B/10% L-lactic acid (88%) | 56 | 70 | 76 | 73 | 79 | | 71 |
| | | 85% C9/10% Emulsifier B/5% L-lactic acid (88%) | 73 | 80 | 86 | 85 | 88 | | 82 |
| 3 | (1.40%, v/v) at 40 gpa | 82% C8/6% lactic/6% e536/6% EmulsB | 48 | 59 | 68 | 68 | | | 61 |
| | | 82% C9/6% lactic/6% e536/6% EmulsB | 55 | 71 | 78 | 73 | | | 69 |
| | | 85% C9/10% EmulsB/5% lactic acid | 56 | 68 | 76 | 74 | | | 69 |
| 3 | (1.40%, v/v) at 20 gpa | 82% C8/6% lactic/6% e536/6% EmulsB | 24 | 29 | 34 | 48 | | | 34 |
| | | 82% C9/6% lactic/6% e536/6% EmulsB | 36 | 49 | 56 | 59 | | | 50 |
| | | 85% C9/15% EmulsB | 36 | 45 | 53 | 66 | | | 50 |
| 4 | (1.40%, v/v) at 40 gpa | 85% C9/15% EmulsB | 53 | 67 | 75 | | | | 65 |
| | | 85% C9/15% EmulsB + 0.25% succinic acid | 64 | 77 | 82 | | | | 74 |
| | | 85% C9/15% EmulsB + 0.284% lactic acid | 72 | 83 | 82 | | | | 79 |
| 4 | (1.40%, v/v) at 20 gpa | 85% C9/15% EmulsB | 41 | 53 | 63 | | | | 52 |
| | | 85% C9/15% EmulsB + 0.25% succinic acid | 55 | 66 | 77 | | | | 66 |
| | | 85% C9/15% EmulsB + 0.284% lactic acid | 59 | 70 | 75 | | | | 68 |

EXAMPLE 28

Comparison of Scythe and Experimental Formulations (C-9 Emulsified with PE 1198+/−L-lactic acid) at Low Application Rates, as Crop Desiccants for Potato Segments (eyes) of seed potato were planted in BACCTO professional potting mix (Michigan Peat Co., P.O. Box 980129, Houston, Tex. 77089) in separate 8-10 inch clay pots. The plants were grown in a greenhouse at 25+/−2 C with supplemental sodium vapor lights providing a noon time intensity of 1,000 µmol m$^{-2}$s$^{1}$ photon flux with a 16 h day/8 h night. The plants were watered and fertilized with a 20-20-20: NPK solution as needed.

Experimental treatments were applied as foliar applications to potato plants. At time of treatments, plants were at five to six inches in height. A single application of treatments was made at 376 L/ha at 276 kPa (40 gallons per acre at 25 psi) to plants at the onset of senescence (1$^{st}$ indication of foliage yellowing and vine laying) using a calibrated track sprayer. A relatively low application rate (1.40%, v/v) was used to properly distinguish treatment effects and relative potency of formulations.

Desiccation or plant injury ratings (0 to 100% injury) were made at one and two days after treatment (DAT). A completely randomized design with 9 replicates per treatment group was used. Data were subjected to analysis of variance and mean separation for least significant difference (LSD) at the 0.05 level. Although phosphate ester-emulsified fatty acid formulations were superior to Scythe, addition of an organic acid synergist such as L-lactic acid further improved performance. The results are given below in Table 28.

TABLE 28

| Treatments (rates: 1.4%, v/v) in water | Average, 2 ratings (0-100% desiccation) |
| --- | --- |
| Control (no treatment) | 0 d |
| Scythe | 4 c |
| 85% C-9/15% phosphate ester emulsifier (PE 1198) | 19 b |
| 85% C-9/5% phosphate ester emulsifier (PE 1198)/10% L-lactic acid | 33 a |

Ratings were taken on day 1 and day 2 after application of treatments and averaged.
Statistically significant (P at 0.05) treatment differences are shown when letters, adjacent to values for percent injury are different.

EXAMPLE 29

Fatty Acid-Based Formulations (with or without Organic Acids) Emulsified with Phosphate Esters The propagation of potato plants in the greenhouse, application of treatments and evaluation of desiccation (percent plant injury) were carried out as described in Example 28. A relatively low application rate (2.0%, v/v) was used to properly distinguish treatment effects and relative potency of formulations. Glycolic acid as a synergist for pelargonic acid (C-9) and Exacto 390, an adjuvant made by Exacto Corporation, each enhanced the performance of the C-9 formulations emulsified with a phosphate ester (PE). The results of this study provided below in Table 29, further illustrate the efficacy of the fatty acid-based formulations emulsified with PE as harvest aids for potato.

TABLE 29

| Treatments (v/v, in water) | Actual Concentration of ingredients in Water | Plant Injury |
| --- | --- | --- |
| 2.0% MS 13 | 1.7% C8/0.3% Klearfac AA270 | 24 |
| 2.0% MS 25 | 1.7% C9/0.3% Klearfac AA270 | 34 |
| 2.0% MS 25 + 0.063% Exacto 390 | 1.7% C9/0.3% Klearfac AA270/0.063% Exacto 390 | 43 |
| 2.0% MS 25 + 0.5% Succinic Acid | 1.7% C9/0.3% Klearfac AA270/0.5% Succinic Acid | 37 |
| 2.0% MS 25 + 0.5% Glycolic Acid | 1.7% C9/0.3% Klearfac AA270/0.35% Glycolic Acid | 41 |
| 2.0% (85% C9/5% PE 1198/10% L-lactic acid | 1.7% C9/0.1% PE 1198/0.18% L-lactic acid | 54 |
| Control (untreated) | | 0 |

Rating scale (0-100% injury: foliage, stems, vines): average of two evaluations
MS 13 = 85% C8/15% BASF Klearfac AA270
MS 25 = 85% C9/15% BASF Klearfac AA270
Multi-replicates/treatment group . . . Single application of treatments at 40 gallons/acre (25 psi)
AA270 and PE 1198 are phosphate ester emulsifiers made by BASF and Huntsman Chemical, respectively.

EXAMPLE 30

Defoliation of Cotton (Delta Pine NuCotn 33B) with Reduced Rates of Ginstar* Enhanced by Experimental C-9 Formulations Seeds of Delta Pine NuCotn 33B were planted in BACCTO professional potting mix (Michigan Peat Co., P.O. Box 980129, Houston, Tex. 77089) in separate 10 inch clay pots. The plants were grown in a greenhouse at 25+/−2 C with supplemental sodium vapor lights providing a noon time intensity of 1,000 µmol m$^{-2}$s$^{1}$ photon flux with a 16 h day/8 h night. The plants (2 per pot) were watered and fertilized with a 20-20-20: NPK solution as needed.

The experimental treatments described below were applied as spray applications to plant foliage. A single application of treatments was made at 564 L/ha (60 gallons per acre) to plants predominantly at open boll. The method for determining leaf drop and a description for the efficacy of fatty acid-based formulations, in the presence of low rates of Ginstar, to considerably enhance cotton defoliation is provided in Table 30. The C-9 formulation contained 85% C-9 (pelargonic acid), 15% emulsifier (PE 1198) and the C-Lactic acid formulation included 85% C-9 (pelargonic acid), 5% emulsifier (PE 1198), and 10% L-lactic acid (88%). SYLGARD® 309 is a non-ionic organosilicone surfactant based on a siloxylated polyether. SYLGARD® is a registered trademark of Dow Corning Corporation, 2200 West Salzburg Road, Midland Mich. 48686-0994,

TABLE 30

| Treatments (v/v, in water) | Total leaf drop** (4 plants) | Activity (Compared to Ginstar, alone) |
| --- | --- | --- |
| Water | 4 | |
| Ginstar* | 15 | 100 |
| Ginstar + 1.5% C-9 | 58 | 387 |
| Ginstar + 1.5% C-9/Lactic acid | 77 | 513 |
| Ginstar + 1.5% C-9 + 0.25% Sylgard 309 | 146 | 937 |

TABLE 30-continued

| Treatments (v/v, in water) | Total leaf drop** (4 plants) | Activity (Compared to Ginstar, alone) |
|---|---|---|
| Ginstar + 1.5% C-9/Lactic acid + 0.25% Sylgard 309 | 204 | 1360 |

*Ginstar applied at 15% of full rate (1.32 ounces/acre) where full rate = 8.8 ounces/acre
**Leaf drop = number of fallen leaves from 4 plants/treatment group where total leaf drop was based on 6 "leaf harvests" (dropped foliage) over 20 days

EXAMPLE 31

Comparison of Scythe and C-8 Formulations Emulsified with Lecithin (with or without Organic Acid) as Herbicides in Replicate Field Trials Carried out on Mixed Weed Species Herbicidal/desiccant activity of experimental formulations described in Table 31 and a commercial pelargonic acid-based product (Scythe, Dow AgroScience) were compared at a field test site with multiple replications of each treatment in a randomized complete block design. Common grass and broadleaf weed species at 8 to 9 inches were used. Plot size was 3 by 6 ft with the experiments repeated over time. Weed species included buckhorn plantain, common dandelion, red and white clover, and bluegrass, each at a height of from about 8 to about 9 inches. A single application of treatments was made at 563 L/ha at 276 kPa (60 gallons per acre at 45 pounds per square inch or psi) to plants using a calibrated backpack sprayer. Ratings of plant injury (0 to 100%) were made at indicated days after treatments. Data were subjected to analysis of variance and mean separation for least significant difference (LSD) at the 0.05 level. The results are provided below in Table 31. Lecithin-emulsified caprylic acid (C-8) formulations were clearly superior to the commercial herbicide Scythe as an herbicide for grasses and broadleaf weed species. LECIPRIME® N is a highly purified soya lecithin product, once available from Riceland Foods, Inc but is now manufactured as Leciprime 1500 by Cargill, Inc.. LECIPRIME® is a registered trademark of Riceland Foods, Inc., P.O. Box 927, Stuttgart, Ill. 72160.

TABLE 31

| Treatment* | Plant Injury** | LSD(0.05)*** |
|---|---|---|
| Scythe | 34 | c |
| 84.5% C-8/1.41% Leciprime N/14.1% mineral oil | 48 | b |
| 84.5% C-8/1.41% Leciprime N/14.1% propionic acid | 63 | a |
| 84.5% C-8/1.41% Leciprime N/14.1% oleic acid | 69 | a |
| Control (no treatment) | 0 | |

*2.5%, v/v, formulation diluted with water
**Average injury rating (2 trials): where injury scale was 0-100% and ratings were made at 2 days after treatment application.
***Least Significant Difference Test where P at 0.05 was utilized. Means within column having similar letters are not significantly different at 5% level.

EXAMPLE 32

Comparison of Scythe with C-8 Formulation (with an Organic Acid and Emulsified with Lecithin) as Herbicides in Replicate Field Trials with Mixed Weed Species The general protocol described in Example 31 was used for the field trial comparison of Scythe with the C-8 formulations described in Table 32. The formulations were examined as candidate herbicides. A single application of treatments at 752 L/ha at 276 kPA (80 gallons per acre at 45 psi) to plant foliage was made. The field trial results (Table 32) confirm previous data (Table 31) that C-8/lecithin/organic acid synergist has improved herbicidal activity over the commercial herbicide, Scythe.

TABLE 32

| Treatment* | Plant Injury** | LSD (0.05)*** |
|---|---|---|
| Scythe | 19 | b |
| 84.5% C-8/1.41% Leciprime N/10% L-lactic acid/4.1% oleic acid | 35 | a |
| 84.5% C-8/1.41% Leciprime N/14.1% L-lactic acid | 41 | a |
| 77.25% C-8/1.70% Leciprime N/16.1% L-lactic acid/4.95% propylene glycol | 33 | a |
| Control (no treatment) | 0 | |

*2.5%, v/v, formulation diluted in water
**Average injury rating (2 trials): where injury scale was 0-100 and ratings were made at 2 days after treatment application.
***Least Significant Difference Test where P was 0.05 was utilized providing means within column having similar letters are not significantly different at 5% level.

As can be seen from the above, one aspect of this present invention provides novel compositions useful for treating plants, and their fruits, vegetables, seeds and/or nuts to prevent or inhibit fungus growth and formation. Methods for using the fungicidal compositions are also provided. The fungicide composition can be used either prophylatically to inhibit and prevent fungus growth and/or to treat existing fungus. It has been determined that the combination of a fatty acid and an organic acid different from the fatty acid provides unexpectedly high fungicidal activity. Further, it has also been determined that fungicidally effective agricultural formulations can be prepared containing as little as 0.01% v/v of the fatty acid but more preferably at 0.1-0.5% v/v. The formulations are effective against a wide spectrum of fungal species. Further the formulations exhibit little or no phytotoxicity toward crop producing plants when applied at fungicidally effective amounts.

A still further aspect of this present invention provides novel compositions useful for killing and/or desiccating unwanted plants and crop plants. Methods for using the herbicidal/desiccant compositions are similarly provided. Applications typically involve post-emergent applications to portions of a plant growing above ground (the leaves and stem). The compositions are particularly suited for initial burn-down in no-till applications, for the complete clearance of a right-away such as an area below power lines, and for spot killing of unwanted weeds about a home or farm. Use of the compositions to selectively kill particular plants can be affected by directing the composition's application onto unwanted plants and away from desirable plants. The compositions are typically non-toxic and readily degrade in the environment.

The present invention contemplates modifications to the fungicide and herbicide formulations as would occur to those skilled in the art without departing from the spirit of the present invention including combining the fungicide and/or herbicide formulations with other agriculturally acceptable components either active or inactive. In addition, the fungicide and herbicide formulations can be applied by various application methods, and at differing rates and on different plants as would occur to those skilled in the art.

What is claimed is:

1. A pesticide composition consisting essentially of a fatty acid, or a salt thereof having between 5 and 22 carbon atoms included in a pesticidally effective amount; an organic carboxylic acid, or a salt thereof, different from the fatty acid, and an emulsifier said composition exhibiting a synergistic pesticidal effect upon application.

2. The composition of claim 1, further including an additive selected from the group consisting of an adjuvant, a diluent, and a combination thereof.

3. The composition of claim 2, wherein said composition is a herbicide and said organic carboxylic acid selected from the group consisting of: acrylic acid, alanine, arginine, aspartic acid, ascorbic acid, asparagine, benzoic acid, bionic acid, cinnamic acid, citric acid, cysteine, formic acid, fulvic acid, fumaric acid, galactonic acid, gluconic acid, glutamic acid, glutamine, glutaric acid, glyceric acid, glycine, glycolic acid, hexonic acid, histidine, humic acid, isobutyric acid, isocitric acid, isoleucine, itaconic acid, ketoglutaric acid, lactic acid, leucine, lysine, methionine, mevalonic acid, malonic acid, oxalacetic acid, pentonic acid, phenylalanine, proline, propionic acid, pyruvic acid, proline, trichloroacetic acid, tetrahydrofurfuryl salicylic acid, saccharic acid, salicylic acid and other salts of salicylic acid, serine, succinic acid, tartaric acid, threonine, tryptophan, tyrosine, valine and mixtures thereof.

4. The composition of claim 3 including the fatty acid in an amount between about 30% v/v and about 99.5% v/v, based upon the total volume of the composition.

5. The composition of claim 3 wherein the fatty acid is selected from the group consisting of: arachidic acid, arachidonic acid, behenic acid, decanoic acid, erucic acid, heptanoic acid, hexanoic acid, lauric acid, linoleic acid, linolenic acid, margaric acid, myristic acid, nonanoic acid, octanoic acid, oleic acid, palmitic acid, palmitoleic acid, pentadecanoic acid, pentanoic acid, stearic acid, undecanoic acid, and mixtures thereof.

6. The composition of claim 2 wherein the composition is a herbicide and the organic carboxylic acid includes an alkyl group attached to a carboxylate group and said alkyl group is a straight chain, branched chain or cyclic alkyl group.

7. The composition of claim 3 wherein the fatty acid is octanoic acid or nonanoic acid.

8. The composition of claim 7 wherein the organic carboxylic acid is selected from the group consisting of: citric acid, gluconic acid, glycolic acid, lactic acid, propionic acid, succinic acid, tartaric acid, and mixtures of these acids.

9. The composition of claim 3 including the organic carboxylic acid in an amount between about 1% v/v and about 50% v/v based upon the total volume of the composition.

10. The composition of claim 3 including the emulsifier in an amount between about 0.5% v/v and about 70% v/v based upon the total volume of the composition.

11. The composition of claim 3 including the fatty acid and the organic carboxylic acid in a weight ratio of between about 1:1000 and about 1000:1.

12. The composition of claim 3 including the fatty acid and the organic carboxylic acid in a weight ratio of between about 1:5 and about 5:1.

13. The composition of claim 2 wherein the composition is a herbicide and the organic carboxylic acid is a dicarboxylic acid.

14. The composition of claim 2 wherein the composition is a herbicide and the organic carboxylic acid is an aromatic carboxylic acid.

15. The composition of claim 2 wherein the composition is a herbicide and the organic carboxylic acid is a monocarboxylic acid.

16. The composition of claim 3 wherein the organic carboxylic acid includes a hydroxyl substituent.

17. The composition of claim 3 including one or more of an adjuvant and/or a diluent.

18. The composition of claim 2 wherein said additive is a diluent and said diluent is selected from the group consisting of: kerosene, xylene, mineral oil, vegetable oil, seed oil, alcohol and a combination thereof.

19. The composition of claim 3 provided as a concentrate suitable for dilution, said composition including said emulsifiers selected to suspend the fatty acid and the organic carboxylic acid in water upon dilution to form a ready-to-use formulation.

20. The composition of claim 3 provided as a ready-to-use crop desiccant or harvest aid formulation suitable for application to a crop prior to or after harvest.

21. The composition of claim 3, wherein said emulsifier is selected from the group consisting of alkanolamides, alkoxylated triglycerides, alkyl benzene sulfonates, alkyl phenol ethoxylates, alkyl polyglycosides, anionic-nonionic mixtures, EO-PO block polymers, ethoxylated fatty alcohols, ethoxylated fatty amines, ethoxylated tristyrylphenols, fatty acid PEG esters, fatty alcohol ether sulfates, lecithins, naphthalene sulfonate condensates, phosphate esters, polyol esters, quaternary amine derivatives, sorbitan esters, and combinations thereof.

22. The composition of claim 3, wherein said fatty acid is nonanoic acid, said organic carboxylic acid is lactic acid, and said emulsifier is a phosphate ester.

23. The composition of claim 22, wherein said phosphate ester is a nonionic phosphate ester selected from the group consisting of aryl-based phosphate esters, linear alcohol phosphate esters and alcohol alkoxylate phosphate esters.

24. A method for controlling plant growth, said method comprising contacting said plant with an effective amount of a ready-to-use composition prepared by diluting the composition of claim 3 with water.

25. A method of controlling plant growth or causing plant desiccation, said method comprising applying to said plant the herbicidal composition of claim 1.

26. The method of claim 25, wherein said plant is a grass.

27. The method of claim 26, wherein said grass is selected from the group consisting of barnyard grass, bluegrass, buffalograss, crabgrass, fall panicum, fescue, foxtail, goosegrass, johnsongrass, nutsedge, oatgrass, orchardgrass, quackgrass, ryegrass, wildproso millet, witchgrass, and combinations thereof.

28. The method of claim 25, wherein said plant is a broadleaf.

29. The method of claim 28, wherein said broadleaf is selected from the group consisting of black medic, broadleaf plantain, buckhorn plantain, bull thistle, chicory, chickweed, common burdock, common cocklebur, common ivy, common lambsquarter, common mallow, common purslane, clover, dandelion, Eastern black nightshade, horsenettle, horseweed, jimsonweed, ladysthumb, milkweed, Pennsylvania smartweed, poison ivy, prickly lettuce, prickly sida, ragweed, redroot pigweed, sheperd's-purse, sunflower, velvetleaf, wild buckweed, wild carrot, wild mustard, yellow rocket, and combinations thereof.

30. The method of claim 25, wherein the plant is selected from the group consisting of velvetleaf, foxtail, common lambsquarter, barnyard grass, chickweed, clover, dandelion, buckhorn plantain, and wild carrot.

31. The method of claim 25, wherein said method of controlling said plant growth includes desiccating said plant prior to or after harvesting said crop.

32. The method of claim 31, wherein said plant is selected from the group consisting of canola, cotton, dry bean, dry pea, onion, potato, seed alfalfa, seed grass, soybean, sugarcane and tomato.

33. The method of claim 25, wherein said composition is applied at a rate ranging from about 0.10 to about 1000 pounds per acre.

34. The method of claim 25, wherein said composition is a diluted form, diluted in a carrier.

35. A herbicide composition consisting essentially of a fatty acid, or a salt thereof having between 5 and 22 carbon atoms included in a herbicidally effective amount; an organic carboxylic acid, or a salt thereof, different from the fatty acid, and an emulsifier wherein said carboxylic acid is selected from the group consisting of glycolic acid, propionic acid, lactic acid, succinic acid salicylic acid, and other salts of salts of salicylic acid, citric acid, tartaric acid and mixtures thereof, said composition exhibiting a synergistic herbicidal effect upon application.

36. The herbicide composition of claim 35, further including an additive selected from the group consisting of an adjuvant, a diluent, and a combination thereof.

37. A herbicide composition consisting essentially of a fatty acid, or a salt thereof having between 5 and 22 carbon atoms included in a herbicidally effective amount; an organic carboxylic acid, or a salt thereof, different from the fatty acid, and an emulsifier wherein said fatty acid is selected from the group consisting of hexanoic acid, heptanoic acid, octanoic acid, nonanoic acid, decanoic acid and mixtures thereof, said composition exhibiting a synergistic herbicidal effect upon application.

38. The herbicide composition of claim 37, further including an additive selected from the group consisting of an adjuvant, a diluent, and a combination thereof.

39. A herbicide composition consisting essentially of a fatty acid, or a salt thereof having between 5 and 22 carbon atoms included in a herbicidally effective amount; an organic carboxylic acid, or a salt thereof, different from the fatty acid, and an emulsifier wherein said emulsifier is selected from the group consisting of phosphate esters, sorbitan esters, lecithins and combinations thereof, said composition exhibiting a synergistic herbicidal effect upon application.

40. The herbicide composition of claim 39, further including an additive selected from the group consisting of an adjuvant, a diluent, and a combination thereof.

* * * * *